United States Patent [19]

Imai et al.

[11] Patent Number: 5,514,398
[45] Date of Patent: May 7, 1996

[54] FOOD ADDITIVE AND USE THEREOF

[75] Inventors: Yutaka Imai; Tomonari Ogawa; Chiho Tsurumi; Masatoshi Kitagawa; Hidero Tanaka, all of Aichi, Japan

[73] Assignee: Amano Pharmaceutical Co., Ltd., Nagoya, Japan

[21] Appl. No.: 244,661

[22] PCT Filed: Oct. 6, 1992

[86] PCT No.: PCT/JP92/01299

§ 371 Date: Jun. 6, 1994

§ 102(e) Date: Jun. 6, 1994

[87] PCT Pub. No.: WO94/07378

PCT Pub. Date: Apr. 14, 1994

[51] Int. Cl.$^6$ .................................................. A23D 7/00
[52] U.S. Cl. ........................... 426/271; 426/601; 426/605
[58] Field of Search ................................ 426/271, 605, 426/601

[56] References Cited

U.S. PATENT DOCUMENTS

| | | | |
|---|---|---|---|
| 3,630,754 | 12/1971 | Wayne | 426/481 |
| 3,667,523 | 6/1972 | Lynn | 426/481 |
| 3,852,504 | 12/1974 | Mihara | 426/478 |
| 4,707,472 | 11/1987 | Inagaki | 514/58 |
| 4,794,014 | 12/1988 | Siren | 426/271 |
| 5,063,070 | 1/1991 | Klemann | 426/271 |
| 5,064,668 | 11/1991 | Klemann | 426/271 |

FOREIGN PATENT DOCUMENTS 60-248611 12/1985 Japan.

OTHER PUBLICATIONS

Journal of the American College of Nutrition, Cheruvanky Rukmini et al, v. 10, No. 6, 1991, pp. 593–601, "Nutritional and Biochemical Aspects of the Hypolipidemic Action of Rice Bran Oil.".

Patent Abstracts of Japan, vol. 6, No. 257 (c–140) 16–Dec.–1982 (JP–A–57150352, Sep. 17, 1982).

Japanese Journal of Nutrition, Oshima et al, vol. 30, No. 5, 1972, pp. 203–205 "Effect of trial–mayonnaise on human serum cholesterol." as reported in Database CAB Abstracts Dialog Accession No. 00177401 (Abstract).

Indian J. Med. Res., Seetharamaiah et al, vol. 92, 1990, pp. 471–475, "Effect of Oryzanol on Cholesterol Absorption & Biliary & Fecal Bile Acids in Rats.".

J. Nutr. Sci. Viaminol., Kiribuchi et al, vol. 29, No. 1, 1983, pp. 35–43, "Hypocholesterolemic effect of Triterpene Alchols with Soysterol on Plasma Cholesterol in Rats.".

*Primary Examiner*—Carolyn Paden
*Attorney, Agent, or Firm*—Sughrue, Mion, Zinn, Macpeak & Seas

[57] ABSTRACT

An additive for cholesterol-containing food, containing a rice bran component and/or a derivative thereof as an active ingredient, a method of using same, and food treated thereby; and a process for producing mayonnaise controlled in the rise of a blood cholesterol level, or the absorption of cholesterol. A method of decreasing the effect of cholesterol contained in food on a living organism, for example, controlling the rise of a blood cholesterol level by adding to cholesterol-containing food a food additive capable of forming a complex with cholesterol, such as an extract of a rice bran component, γ-orizanol (γ-OZ) which is a mixture of esters of ferulic acid with various alcohols prepared by refining said extract and/or a derivative of a rice bran component, thereby forming a cholesterol complex of the food additive, whereby the cholesterol contained in food becomes nonabsorbable by a living organism or can be removed therefrom.

3 Claims, 16 Drawing Sheets

FOOD ADDITIVE AND USE THEREOF

TECHNICAL FIELD

This invention relates to an additive for a cholesterol-containing food which comprises rice bran components and/or derivatives thereof as an active component, use of the same and a food obtained by this method.

More particularly, it relates to a food additive which comprises a rice bran component extract (hereinafter referred to simply as the extract), ferulates of various alcohols obtained by purifying the extract, γ-oryzanol (hereinafter referred to simply as γ-OZ), i.e., a mixture of these esters, and/or derivatives of the rice bran components capable of forming a cholesterol complex; use of the same; and a food which has been prepared by this method which forms a cholesterol complex.

BACKGROUND ART

In recent years, an increase in cholesterol intake accompanying the diversification in our eating habits has become a serious social problem in connection with diseases. Namely, we frequently eat foods of a high cholesterol content these days. As a result, cholesterol contained in these foods elevates the blood cholesterol level, which is the major cause of, for example, arteriosclerosis.

To lower the cholesterol content in these foods, there have been reported some methods for decomposing cholesterol with the use of cholesterol oxidase.

Rice bran contains a number of components. For example, γ-OZ, which is prepared by purifying these components, is a mixture of ferulates of various vegetable sterols and triterpene alcohol. For example, γ-OZ consists of 14% of campesterol ferulate, 1% of stigmasterol ferulate, 4% of β-sitosterol ferulate, 2% of cycloartanol ferulate, 35% of cycloartenol ferulate and 44% of 24-methylene cycloartanol ferulate.

As examples of the application of γ-OZ to medical purposes, there has been reported that it has pharmacological effects of promoting growth, controlling diencephalic function, lowering serum cholesterol level, increasing amine-like compounds in amygdaloid nucleus and stimulating gonad, and clinical effects of treating menopausal disorders and autonomic imbalance.

Regarding the above-mentioned effect of γ-OZ of lowering serum cholesterol level, its effects on catabolism/excretion of cholesterol in rat has been reported [Geriatric Medicine, vol. 18, 519–524 (1980); Domyakukoka (arteriosclerosis), vol. 11 (2), 411–416 (1983)].

In the field of food, γ-OZ has been employed as an antioxidant. However, since γ-OZ exhibits only a very weak antioxidant effect, it is scarcely used alone but mixed with tocopherol so as to enhance its effect.

Also, it is reported that organic acid esters of triterpene alcohol, namely, derivatives of the main constituent of γ-OZ, are applicable to drugs for treating hyperlipemia (JP-A-61-243022 and JP-A-61-243099; the term "JP-A" as used herein means an "unexamined published Japanese patent application"). Although these drugs aim at treating this disease by preventing an increase in serum cholesterol level or lowering the same, their function mechanisms have not been clarified in detail so far.

As discussed above, γ-OZ or rice bran component derivatives have been studied and applied as drugs. However, no attempt has been made so far to clarify their function per se of directly binding to cholesterol to form a cholesterol complex and they have not been used as a food additive by taking advantage of this function.

Today, mayonnaise is a seasoning which is essentially needed in our westernized eating habits in Japan. In general, mayonnaises are produced by adding edible oils, vinegar, seasonings etc. to egg white and yolk to form an oil-in-water emulsion.

With the recent tendency toward health foods such as low-cholesterol or low-salt foods and a variety of tastes, there have been proposed mayonnaises free from cholesterol or containing cholesterol in a reduced amount which are produced by using no or little egg yolk. For example, JP-A-50-64466 has proposed an egg yolk-free mayonnaise produced by using starch paste and egg white, while JP-A-63-275 has proposed a mayonnaise produced by using soybean flour. Further, JP-A- 60-43347 has proposed a process for producing a mayonnaise having a function of lowering blood cholesterol level or suppressing an increase of the blood cholesterol level, in which monolinolein is added to an edible oil to be used.

Not only chemical seasonings and spices but also egg components, in particular, egg yolk largely contribute to the flavor of mayonnaise. In addition, egg yolk plays an important role in the shape retention when mayonnaise is used in salad dressing placed on salad.

Namely, since mayonnaise has a high acidity due to vinegar which is used in a large amount, a stable emulsion of mayonnaise can hardly be achieved by using common edible emulsifiers and it is highly important to use the emulsifying power of egg yolk.

Thus, it is considered that the use of egg yolk is an essential requirement in the production of mayonnaise.

The conventional mayonnaises being free from egg yolk or containing egg yolk in a reduced amount have no or only deteriorated body taste of egg yolk. Further, they are not satisfactory in shape retention properties as a mayonnaise to be used as a seasoning.

On the other hand, the method of adding monolinolein to fat and oil suffers from a problem that monolinolein is hardly available. In addition, only an unsatisfactory effect of lowering blood cholesterol level is achieved by this method.

DISCLOSURE OF THE INVENTION

The present inventors have conducted extensive studies to solve these problems. As a result, they have found out that rice bran components and/or derivatives thereof have an ability to form a complex with cholesterol and that the complex formed by adding the rice bran components and/or derivatives thereof to a food is not absorbed by a living body, thus suppressing an increase in serum cholesterol level.

The present inventors have further found out that a mayonnaise capable of remarkably suppressing an increase in blood cholesterol level can be produced by using a fat and oil containing rice bran components and/or derivatives thereof in the production of a mayonnaise having an oil-in-water emulsion structure comprising fats and oils, souring agents, whole egg and/or egg yolk, etc. containing cholesterol, and other seasonings and additives required.

They have furthermore found out for the first time that similar effects can be achieved by using whole egg and/or egg yolk treated with rice bran components and/or derivatives thereof and that a mayonnaise, which is produced by using whole egg and/or egg yolk treated with rice bran components and/or derivatives thereof together with fats and oils containing rice bran components and/or derivatives, has a function of further remarkably suppressing an increase in blood cholesterol level. The present invention has been completed based on these findings.

The present invention provides a method for relieving the effects of cholesterol contained in various foods on a living body by converting the cholesterol into another form which is not absorbed by a living body or eliminating the cholesterol from the foods after converting it into another form which is not absorbed.

The present invention further provides a method for producing a mayonnaise which can suppress an increase in the blood cholesterol level, i.e., the absorption of cholesterol, though egg yolk is used in the production of the mayonnaise.

According to the present invention, the absorption of cholesterol by a living body can be prevented and thus an increase in the blood cholesterol level can be prevented by adding an additive, which comprises rice bran components and/or derivatives thereof as an active component and which has an ability to form a cholesterol complex, to a food and thus forming a cholesterol complex together with cholesterol contained in the food, or removing the thus formed cholesterol complex after the addition.

A cholesterol complex means a state where cholesterol has bound to the rice bran component and/or a derivative thereof added to the food, its solubility is largely lowered, and thus the absorption of cholesterol by a living body is prevented. Since such a complex is hardly soluble in solvents, it can be removed as a precipitate from the food by a conventional means. Thus, a food of a reduced cholesterol content can be obtained.

The rice bran components and/or derivatives' thereof to be used in the additive of the present invention also include an extract prepared by extracting the components of rice bran from rice bran by a conventional means. Such an extract can be obtained by, for example, extracting oily components from rice bran with a solvent, degumming, dewaxing and alkali-hydrolyzing these oily components, neutralizing the hydrolyzate, subjecting it to solid/liquid separation and distilling the residue, followed by solvent-extraction and column treatment. As a particular example thereof, the following extraction process may be exemplified.

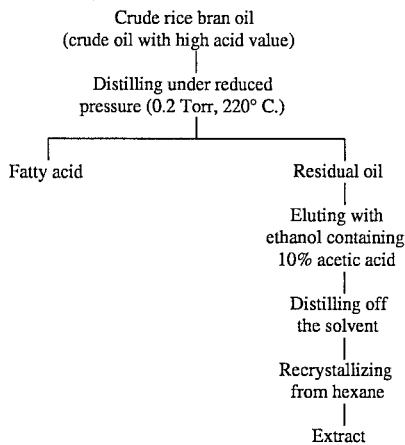

Needless to say, any materials such as an extract which is obtained in each intermediate step of the above method and contains various rice bran components may be used in the present invention, so long as it can form a complex with cholesterol. Furthermore, extracts obtained by any methods other than the above-mentioned one may be used and the degree of purification of the extract may be at an arbitrary level, so long as they can form a cholesterol complex.

In addition, γ-OZ obtained by further purifying the above-mentioned extract as well as its single component thereof obtained by furthermore purifying the same, for example, cycloartenol ferulate (hereinafter referred to simply as CAFE) or 24-methylene cycloartenol ferulate (hereinafter referred to simply as 24-MFE) are also regarded as the rice bran components.

As examples of the derivatives of the rice bran components, esters of triterpene alcohols with α-alkyl($C_1$ to $C_4$)-cinnamic acid having one or two substituents binding to the benzene ring, and esters of triterpene alcohols with cinnamic acid or benzoic acid having two substituents selected from combinations of a $C_1$-$C_4$ alkoxy group with a nitro group, a $C_1$-$C_4$ alkoxy group and an amino group and a $C_1$-$C_4$ alkoxy group with a $C_2$-$C_5$ acylamino group binding to the benzene ring may be cited.

As examples of triterpene alcohol, cycloartenol, cyclobranol and 24-methylene cycloartenol may be cited.

Among these additives, the extract, γ-OZ and CAFE can be preferably used as the rice bran component, while an ester of cycloartenol with 3-methoxy-4-hydroxy-α-methylcinnamic acid, i.e., cycloartenol-α-methylferulate (hereinafter referred to simply as CAMFE) can be preferably used as a rice bran component derivative.

As a matter of course, as an additive, each of the above-mentioned extract, γ-OZ, various components of rice bran and the rice bran component derivatives can be used singly or a mixture of two or more of them can be used.

As particular examples of the food to be used as the subject of the present invention, those containing cholesterol at a higher level compared with other foods and those containing a large amount of cholesterol being condensed in the processing step, though the cholesterol content of the starting material is not relatively high, may be exemplified. In the case of diet foods of limited cholesterol intake, the present invention is applicable to any foods.

As examples of foods of a high cholesterol content, meats, eggs and fish may be cited. Examples of the meats include pork, beef, chicken and their internals. Examples of the eggs include chicken egg, salmon roe, cod roe and herring roe. Examples of the fish include squid, corbicula, eel and shishamo smelt. Further, primary and secondary processed products of these foods, for example, egg yolk powder, mayonnaise, hamburger and cake, are included. As examples of the foods containing a large amount of cholesterol being condensed in the processing step, dairy products such as butter, cheese, cream and milk powder may be cited. The cholesterol content in these final products can be lowered by treating the starting material thereof, for example, cow's milk with the food additive of the present invention.

The term "mayonnaise" to be used herein means a so-called mayonnaise or dressing, and the mayonnaise includes everything produced by conventional methods. That is to say, the mayonnaise means a seasoning which has an acidic pH value and an oil-in-water emulsion structure formed by using egg white and yolk as an emulsifier.

A dressing means a seasoning other than mayonnaises which has an oil-in-water emulsion structure containing egg yolk.

As the fats and oils to be used in the production of the mayonnaise, various edible oils containing, either inherently or artificially, the rice bran components and/or derivatives thereof can be used. As an example of an edible oil inherently containing rice bran components and/or derivatives thereof originating in the starting material, rice oil (unpolished rice germ oil) obtained from rice bran and the like may be exemplified.

Rice oil can be prepared from rice bran, for example, in the following manner. The feedstock rice bran is sieved and ground rice grains are separated. After a pre-extraction treatment, cold extraction and miscella distillation are effected. The crude rice bran oil thus obtained is then centrifuged, degummed, dewaxed, deacidified, decolored and winterized. Thus, a refined rice oil can be obtained.

Now, a concrete example of the preparation process will be given.

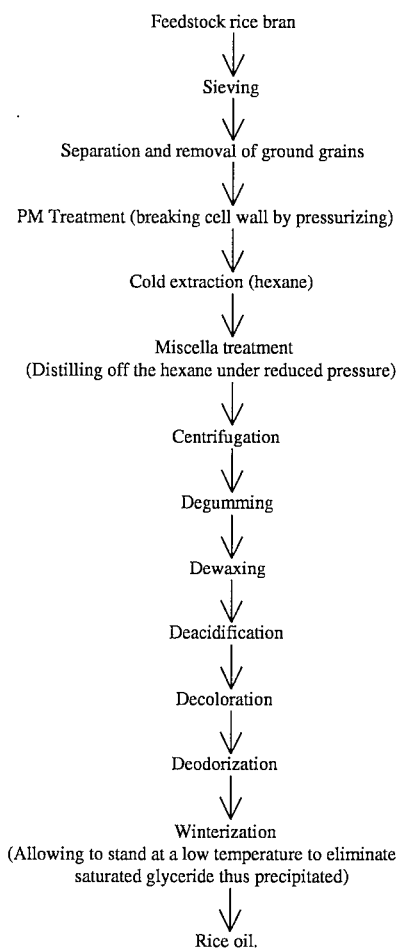

Alternately, fats and oils obtained by adding the rice bran components and/or derivatives thereof to various edible oils may be used.

The edible oil, to which the rice bran components and/or derivatives thereof are to be added, may be arbitrarily selected, so long as it is usable in the production of mayonnaise. For example, corn oil, soybean oil, sunflower oil, rapeseed oil and cottonseed oil may be exemplified.

To produce mayonnaise, the rice bran components and/or derivatives thereof may be preferably used at a ratio of from 0.01 to 10%.

In the method for the production of a mayonnaise in accordance with the present invention, whole egg and/or egg yolk which have been treated with the rice bran components and/or derivatives thereof can be used as the whole egg and/or egg yolk component. Either the whole fresh egg or the yolk alone may be used and a dry egg yolk can be used as the egg yolk. Alternately, an egg yolk powder prepared by treating egg yolk with the rice bran components and/or derivatives thereof followed by freeze-drying may be used.

The addition method varies depending on the form of the food to which the rice bran components and/or derivatives thereof are to be added. Namely, the rice bran components and/or derivatives thereof may be added in the form of a powder or, alternately, in the form of a liquid prepared by using an appropriate medium which has been commonly employed in the production of foods. In order to achieve the direct contact with cholesterol contained in the food, it is preferable to add the rice bran components and/or derivatives thereof in the form of a liquid.

To use as a food additive, the rice bran components and/or derivatives thereof are preferably added in a step during the course of processing the food. After adding the rice bran components and/or derivatives thereof, the food is stirred by an appropriate means. It is enough to stir the food until the formation of the complex is completed. In general, 10 minutes to 24 hours are needed therefor.

To facilitate the contact of a liquid food with the rice bran components and/or derivatives thereof, it is effective to add a step of drying. In this drying step, commonly employed drying means, for example, heat drying or freeze-drying may be employed. Freeze-drying is a preferable method from the viewpoint of maintenance of the qualities of the food.

The rice bran components and/or derivatives thereof are added at a ratio of from 1 to 10 parts by weight, preferably from 2 to 6 parts by weight, per part by weight of cholesterol contained in the food. Although this addition level varies depending on the purity of the additive, it is generally recommended to add the rice bran components and/or derivatives thereof in an amount required for the formation of the complex with cholesterol which is to be eliminated in order to control the cholesterol content in the food to the desired level. Cholesterol and the active component usually undergo the reaction of forming the cholesterol complex at a molar ratio of 1:1.

The rice bran components and/or derivatives thereof capable of forming a cholesterol complex thus added form the cholesterol complex in the food to thereby lower the absorption ratio of cholesterol in a living body. Therefore, it is unnecessary to remove the cholesterol complex. However, the cholesterol complex can be removed from the food by an appropriate method by taking advantage of a difference in solubility between cholesterol and the cholesterol complex. A rice bran extract is preferably used as a food additive from the viewpoint of safety, since it is a natural material which can remain in a food.

BEST MODE FOR CARRYING OUT THE INVENTION

Figure 1:
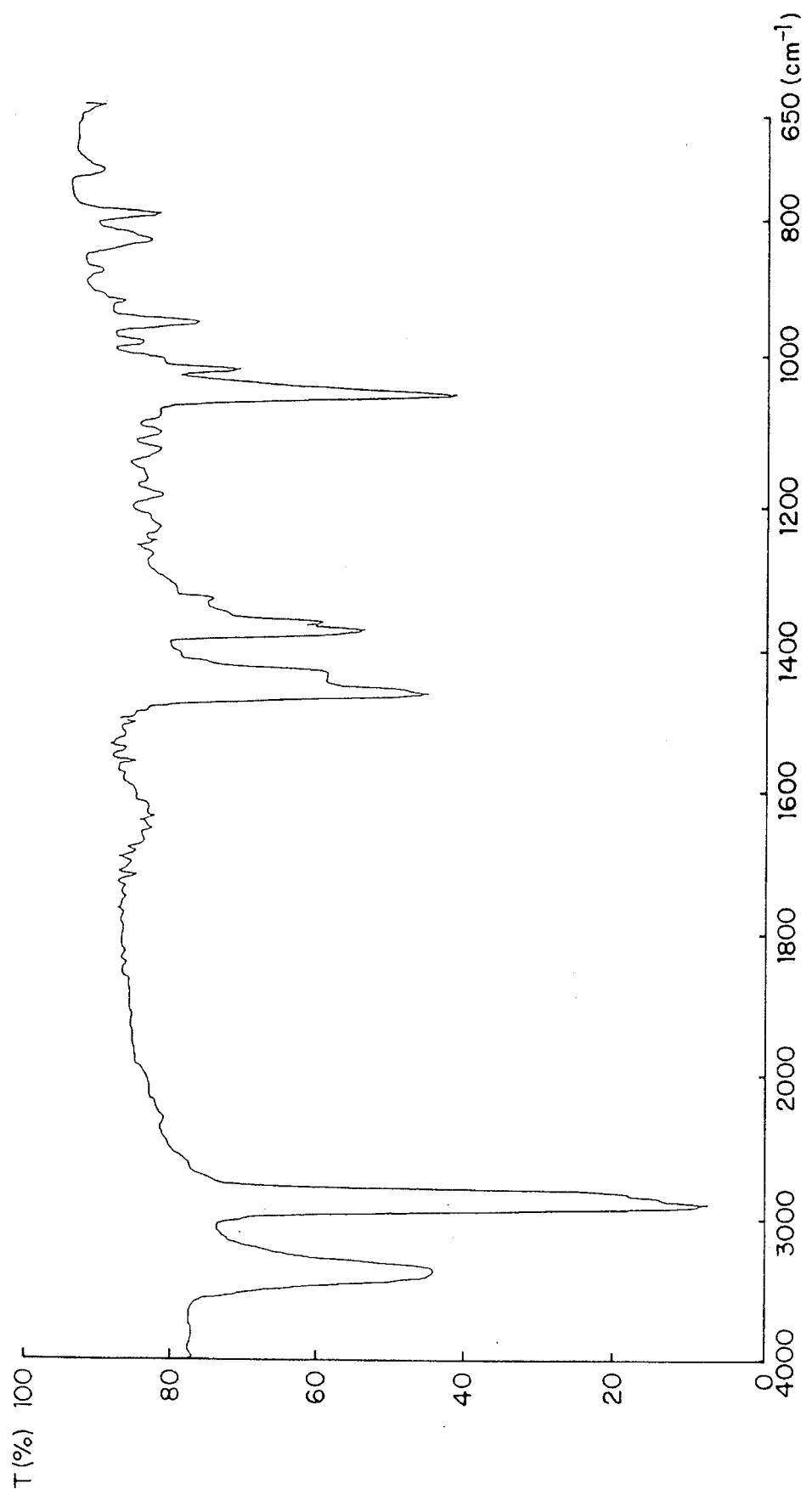
FIG. 1 shows the infrared absorption spectrum of CHL.
Figure 2:
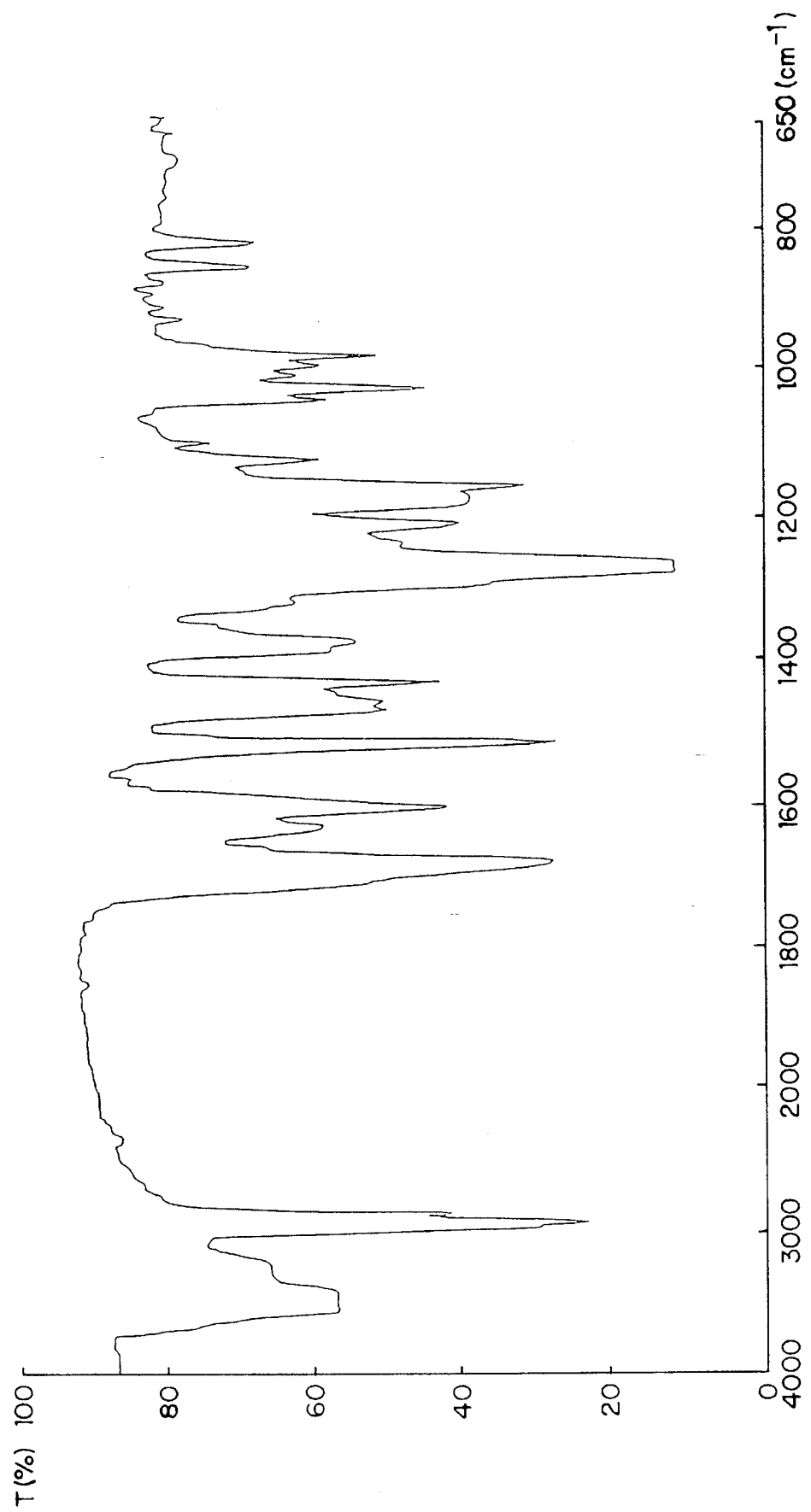
FIG. 2 shows the infrared absorption spectrum of CAFE.
Figure 3:
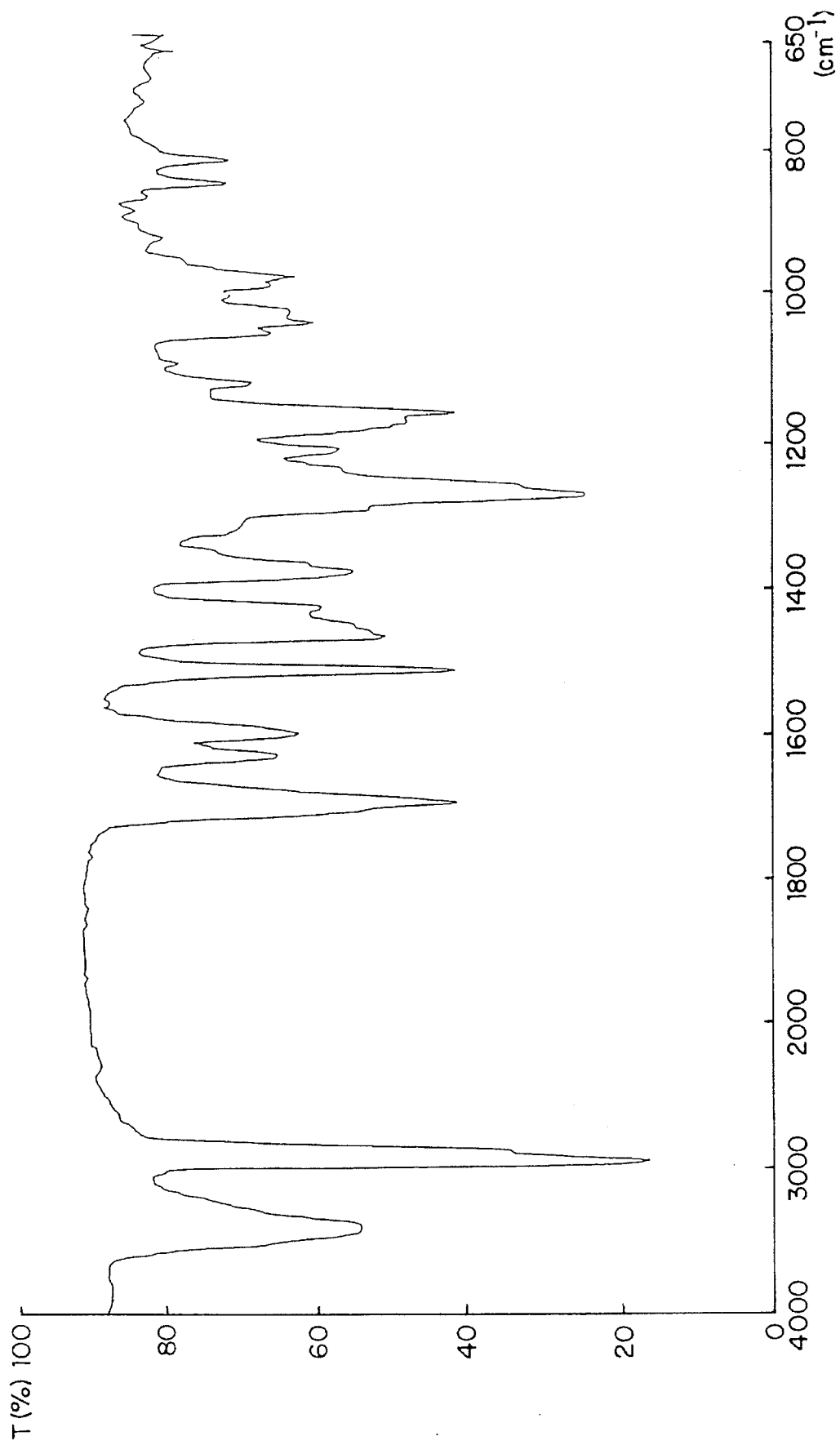
FIG. 3 shows the infrared absorption spectrum of CAFE+CHL.
Figure 4:
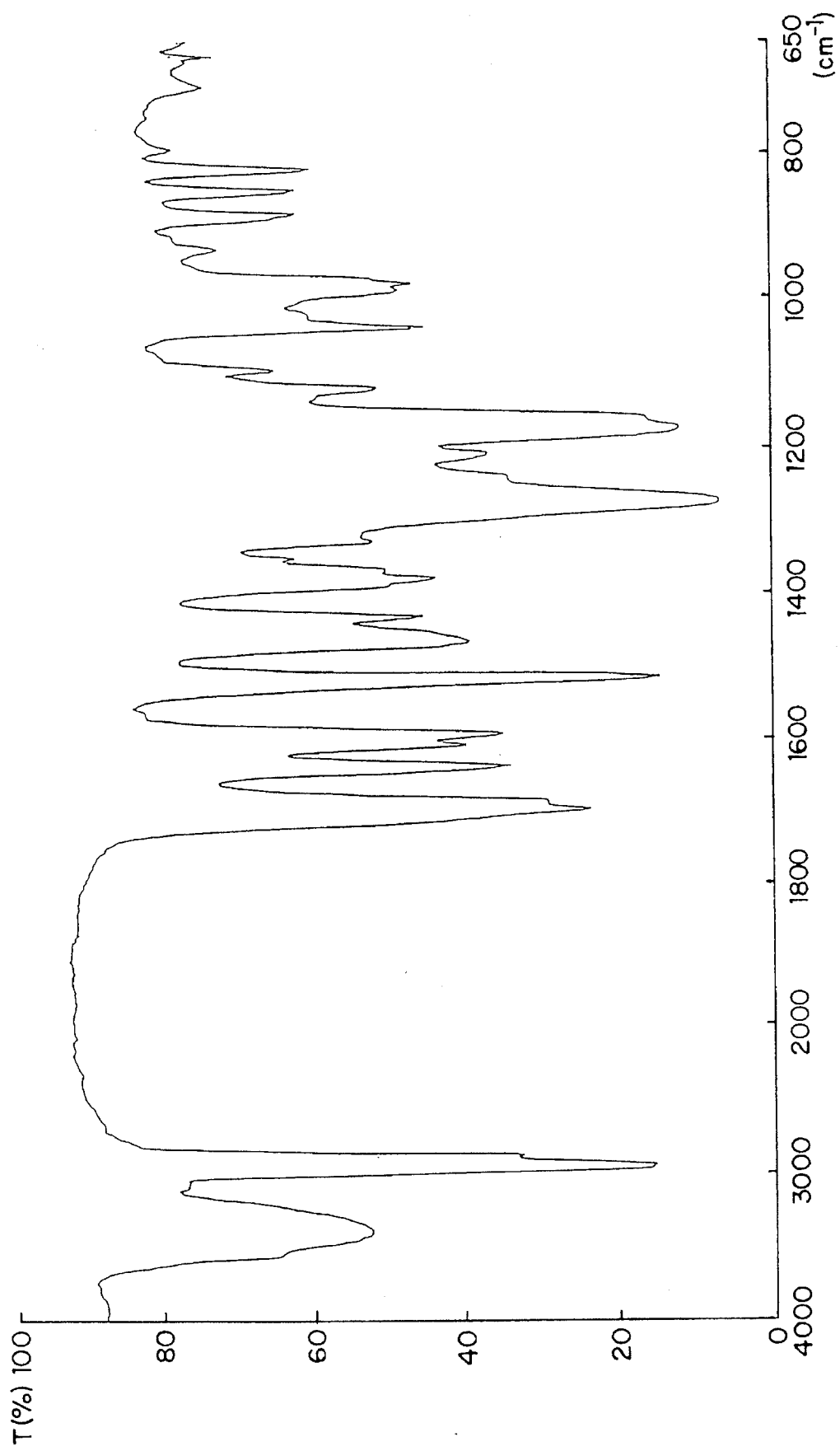
FIG. 4 shows the infrared absorption spectrum of 24–MFE.
Figure 5:
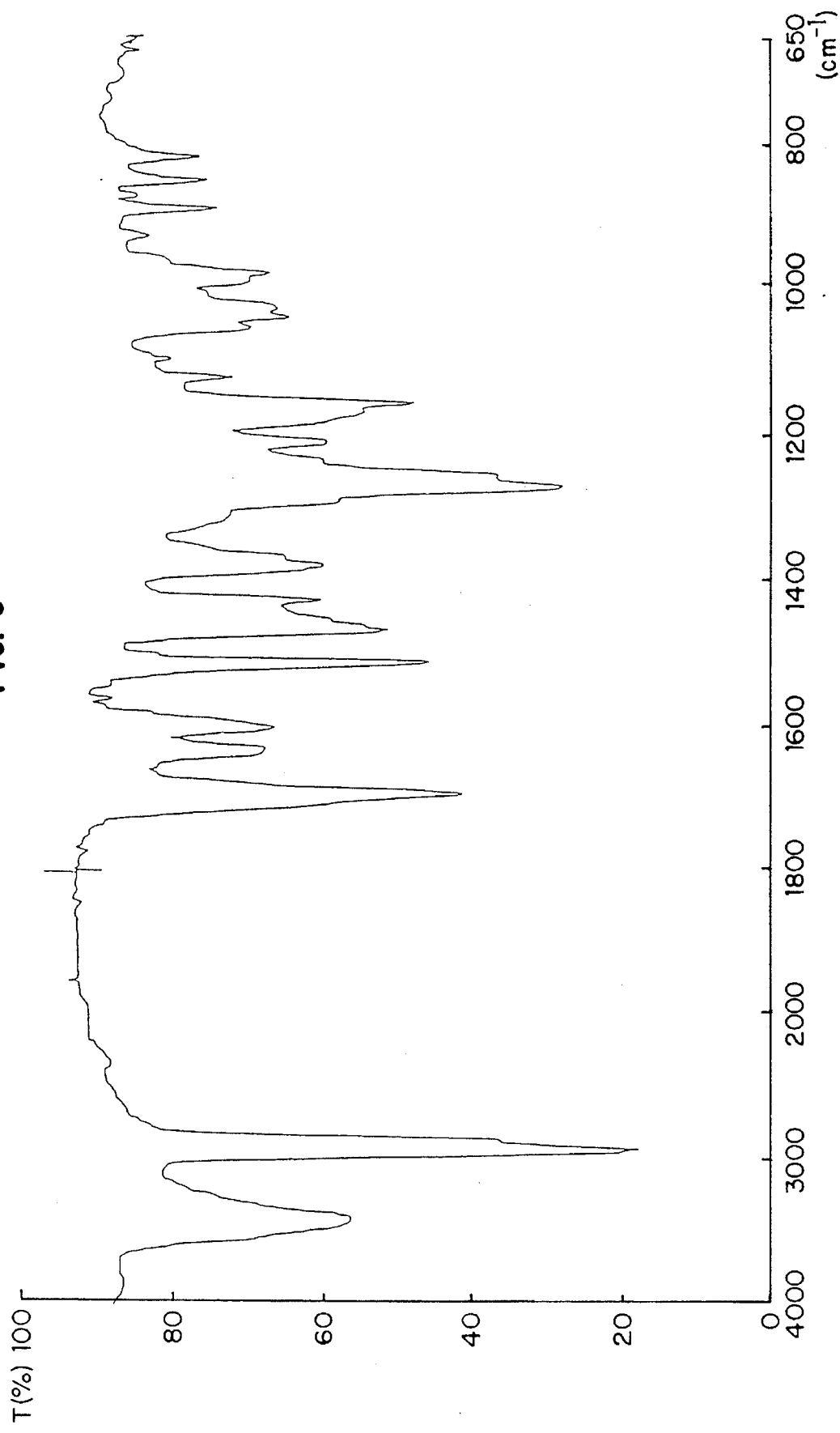
FIG. 5 shows the infrared absorption spectrum of 24–MFE+CHL.
Figure 6:
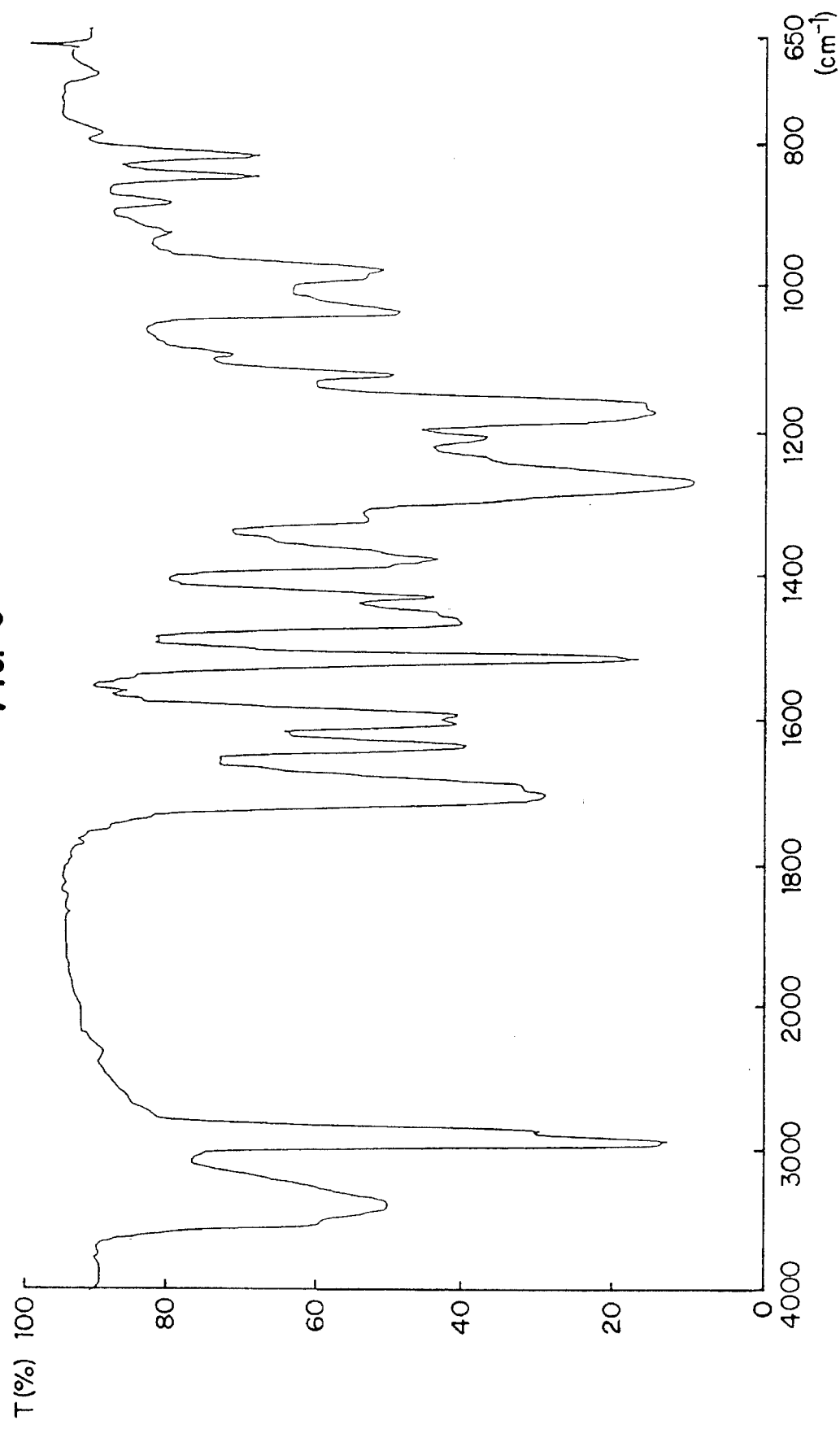
FIG. 6 shows the infrared absorption spectrum of the extract.
Figure 7:
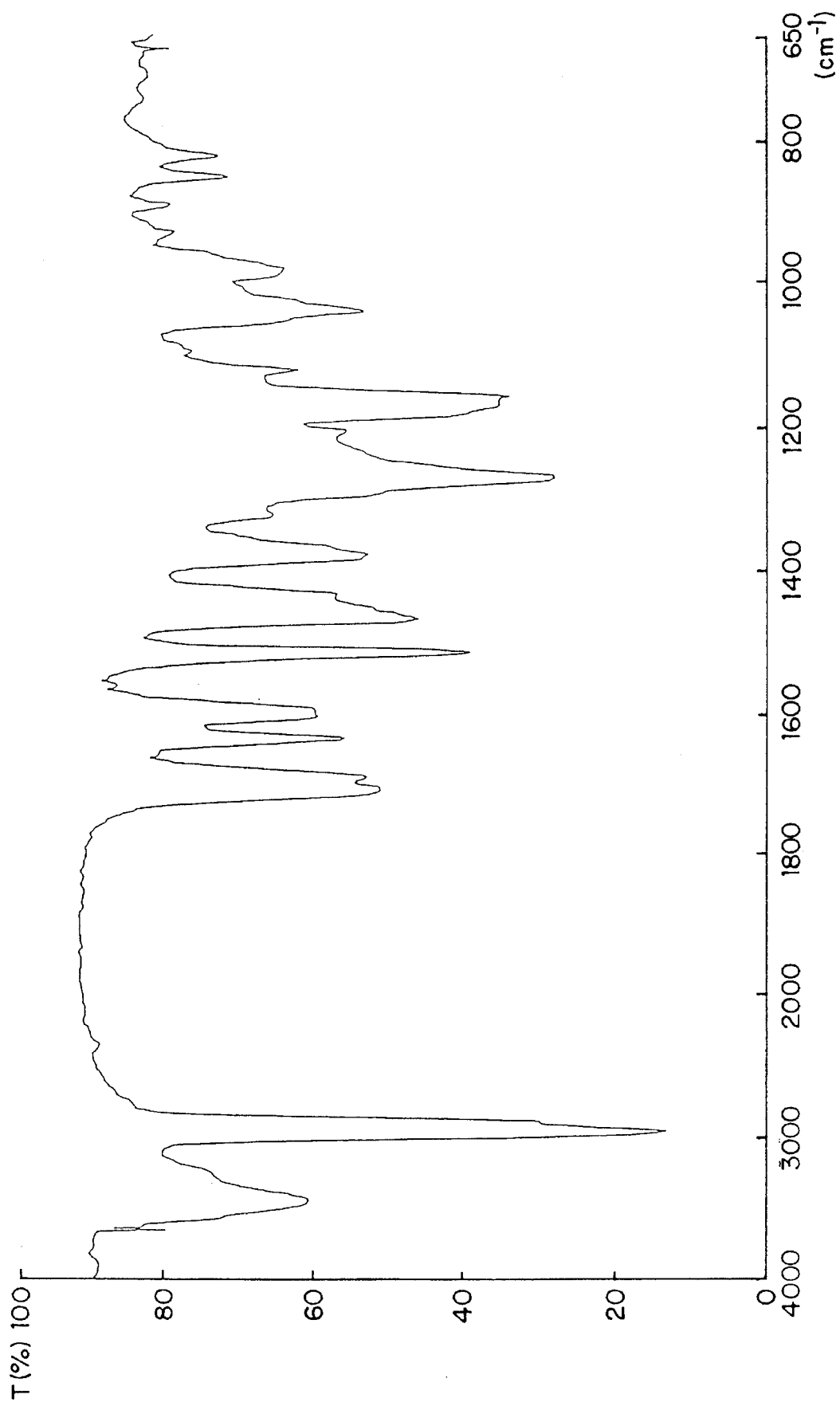
FIG. 7 shows the infrared absorption spectrum of the extract+CHL.
Figure 8:
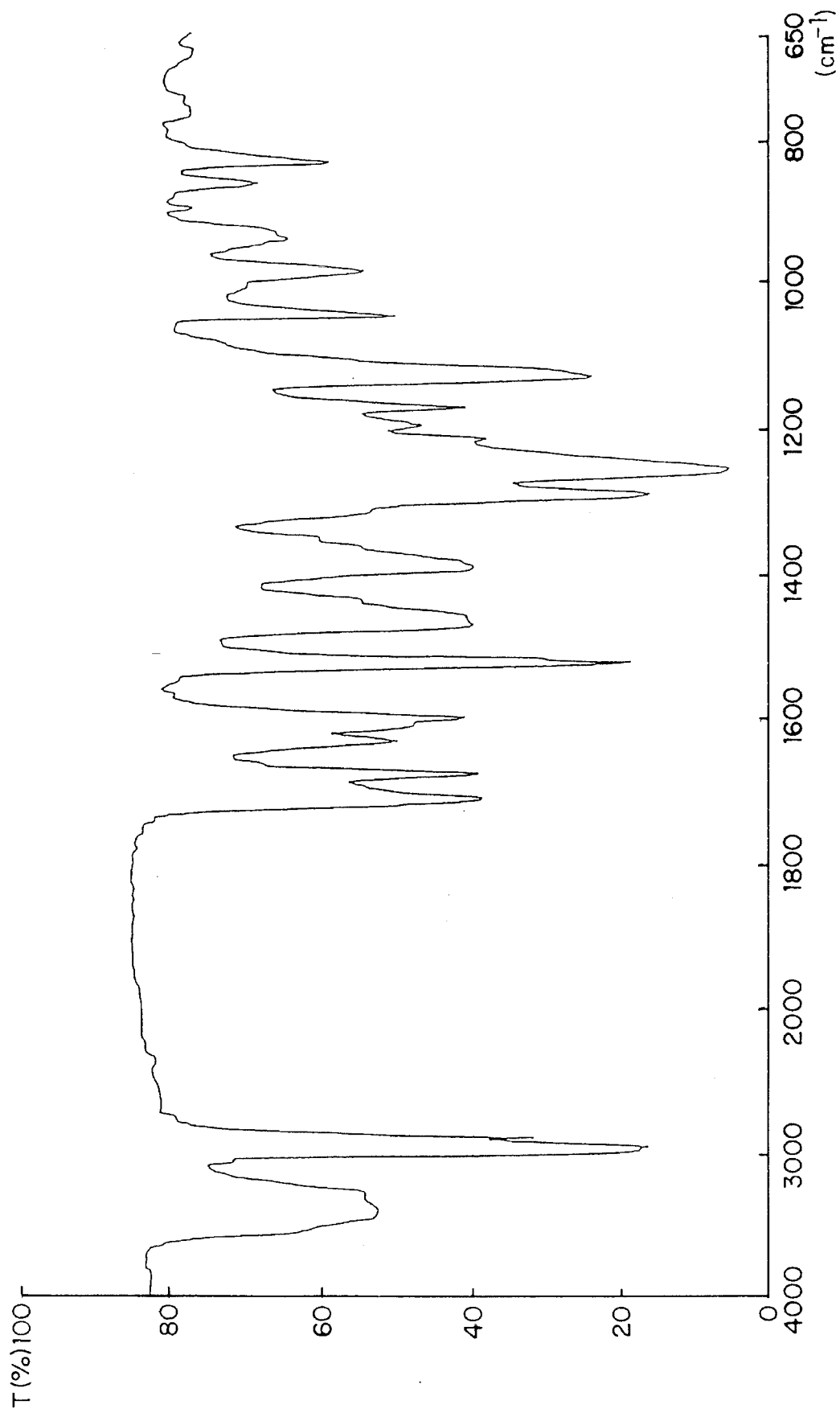
FIG. 8 shows the infrared absorption spectrum of CAMFE.
Figure 9:
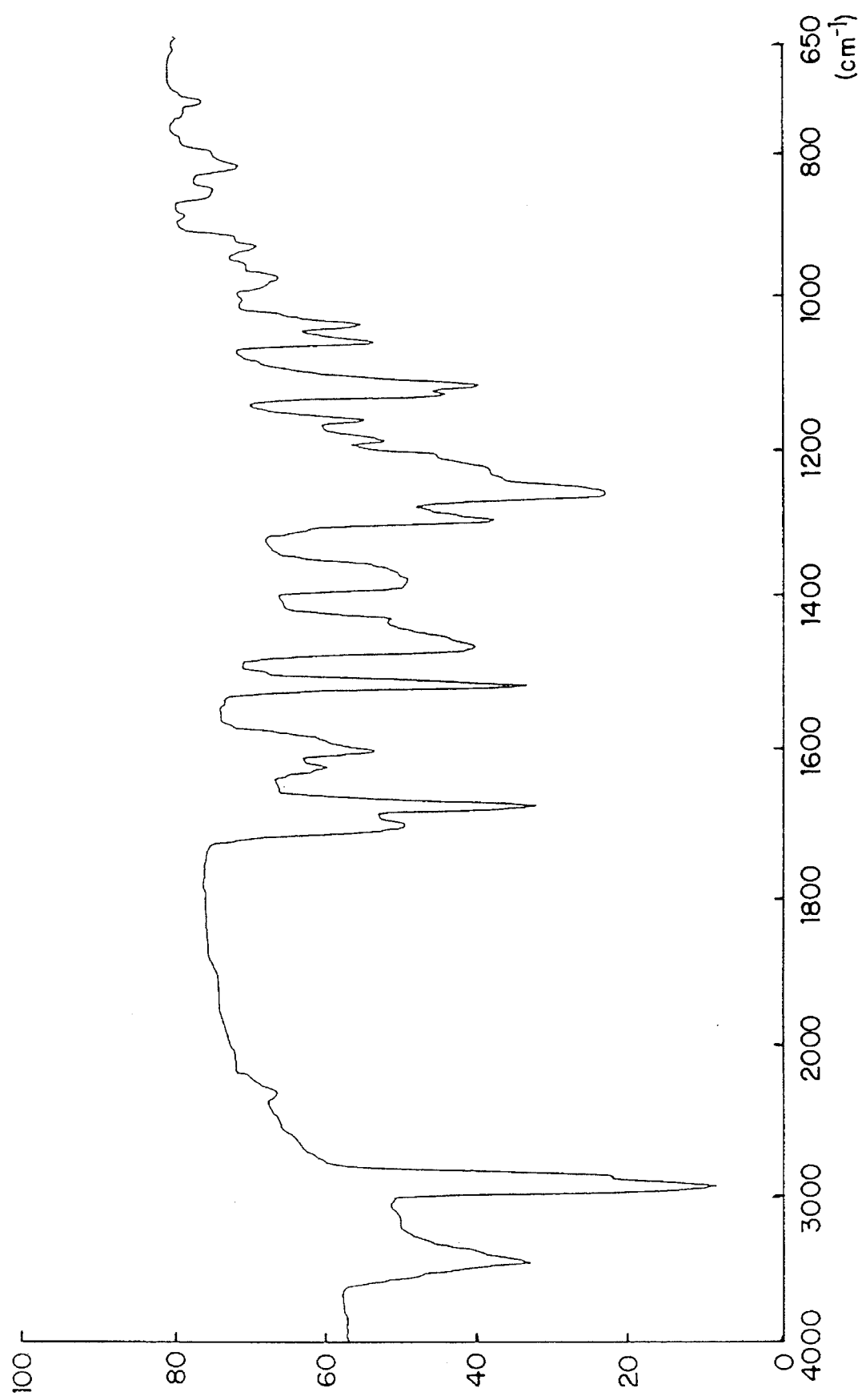
FIG. 9 shows the infrared absorption spectrum of CAMFE+CHL.
Figure 10:
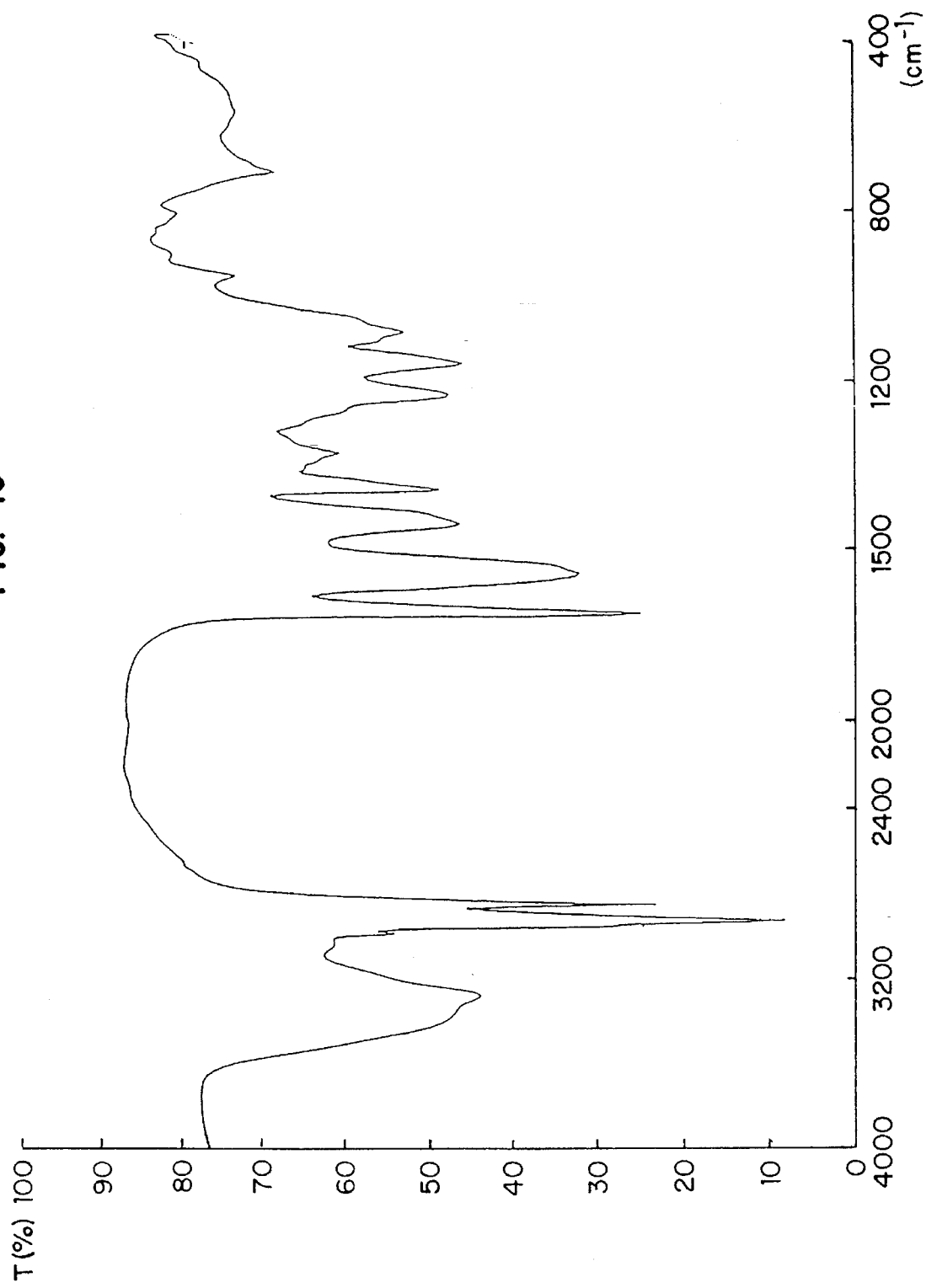
FIG. 10 shows the infrared absorption spectrum of egg yolk.
Figure 11:
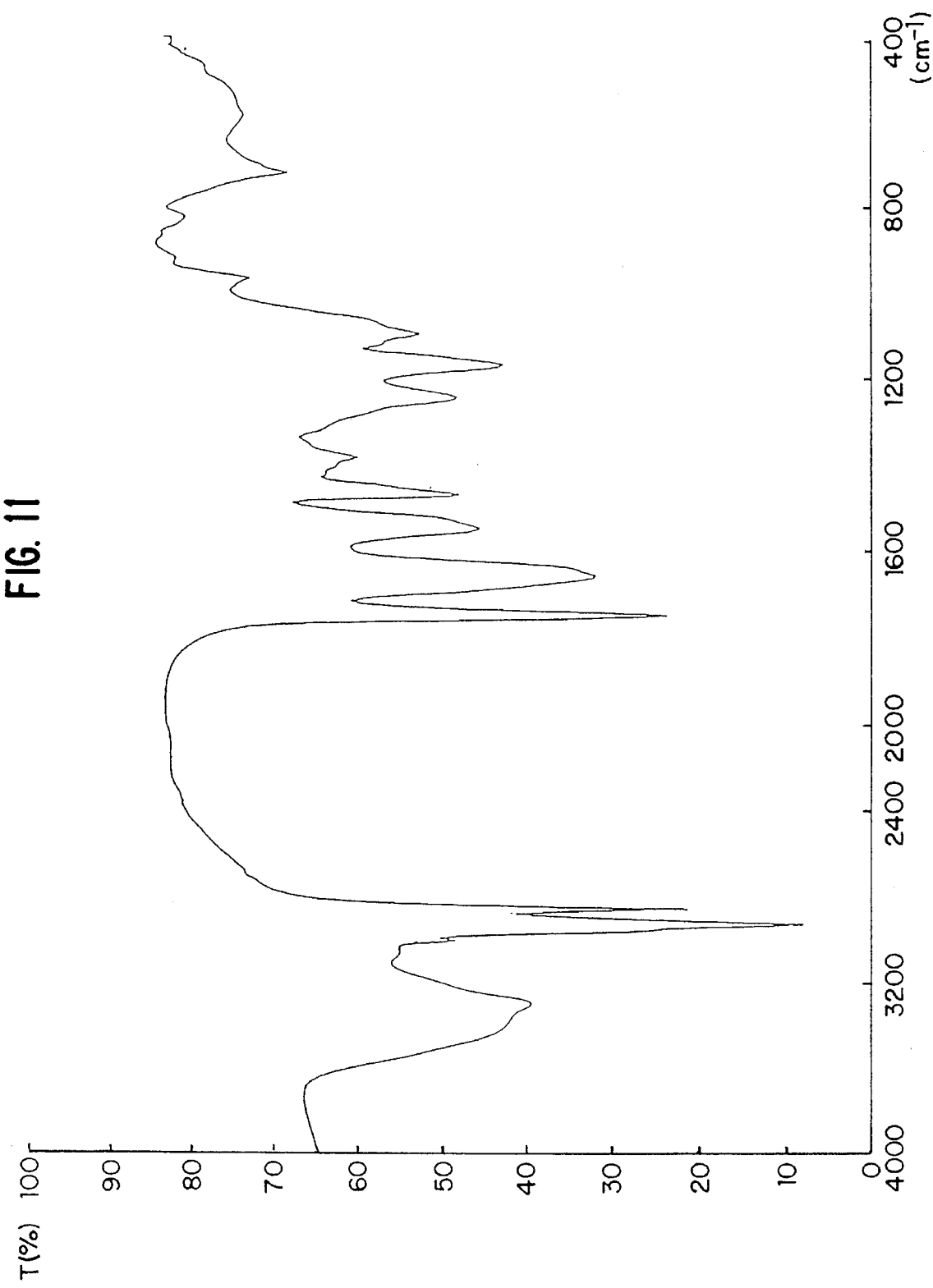
FIG. 11 shows the infrared absorption spectrum of CAFE+egg yolk.
Figure 12:
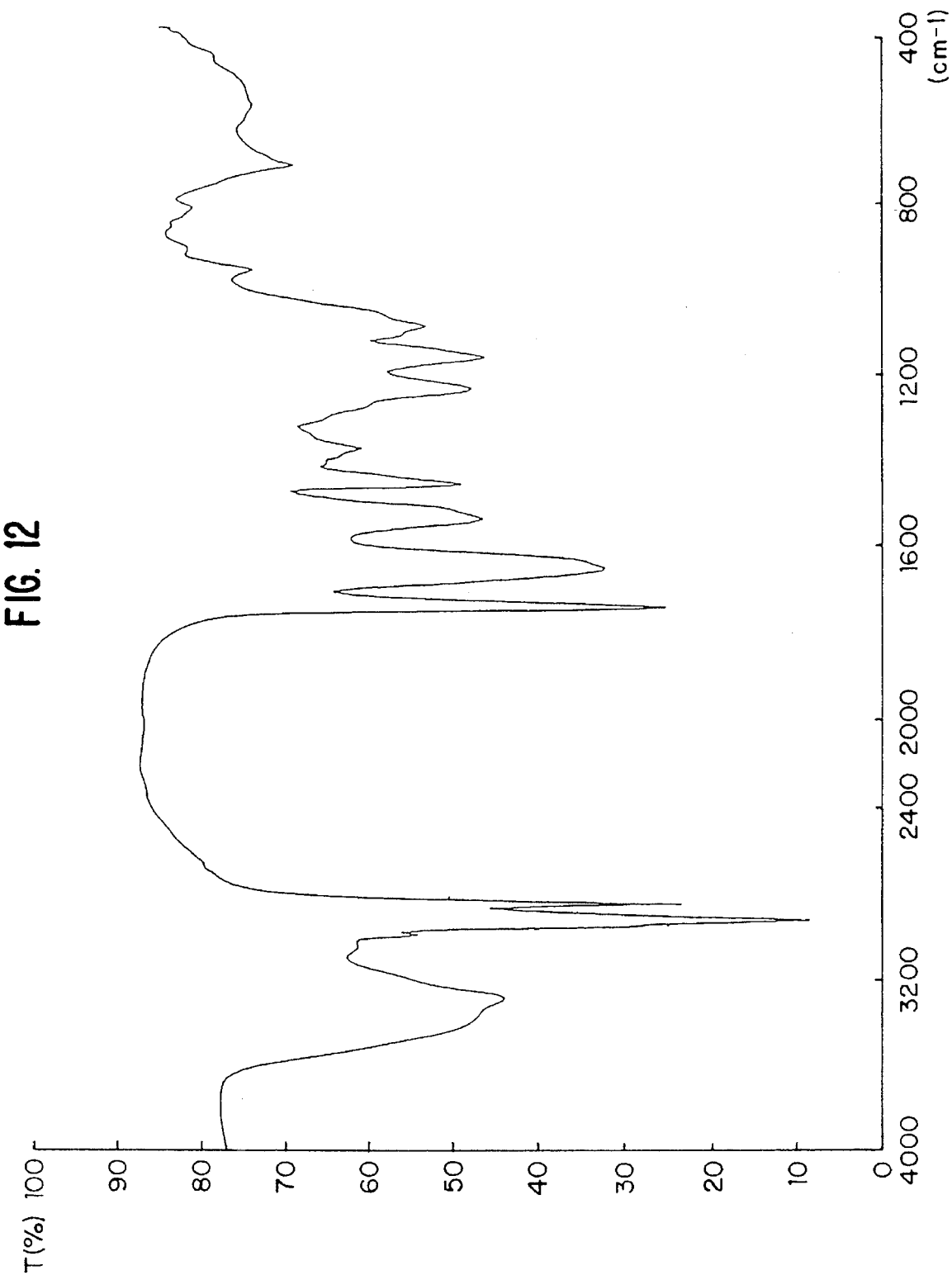
FIG. 12 shows the infrared absorption spectrum of CAMFE+egg yolk.
Figure 13:
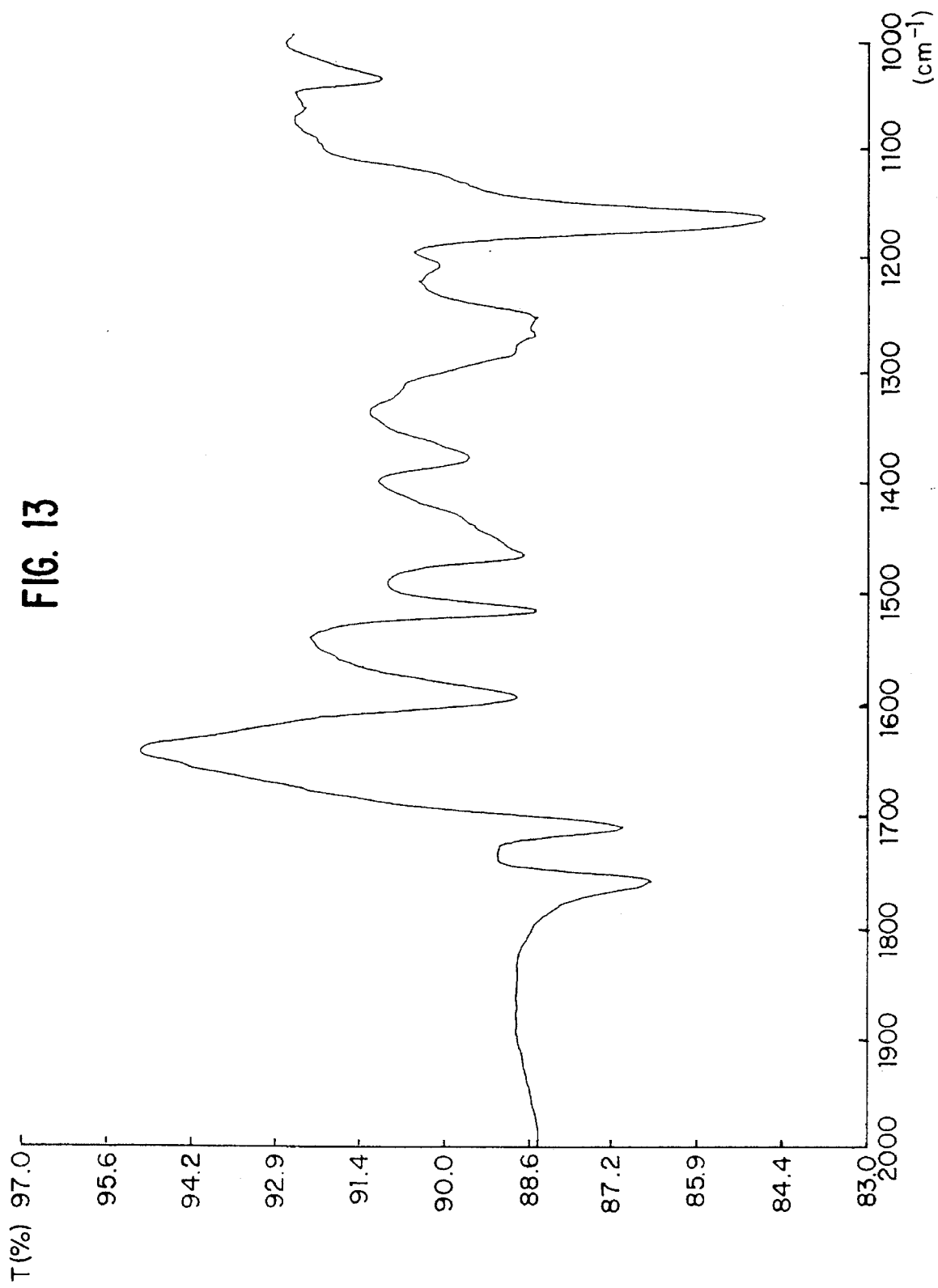
FIG. 13 shows the differential infrared absorption spectrum of CAFE+egg yolk and egg yolk alone.
Figure 14:
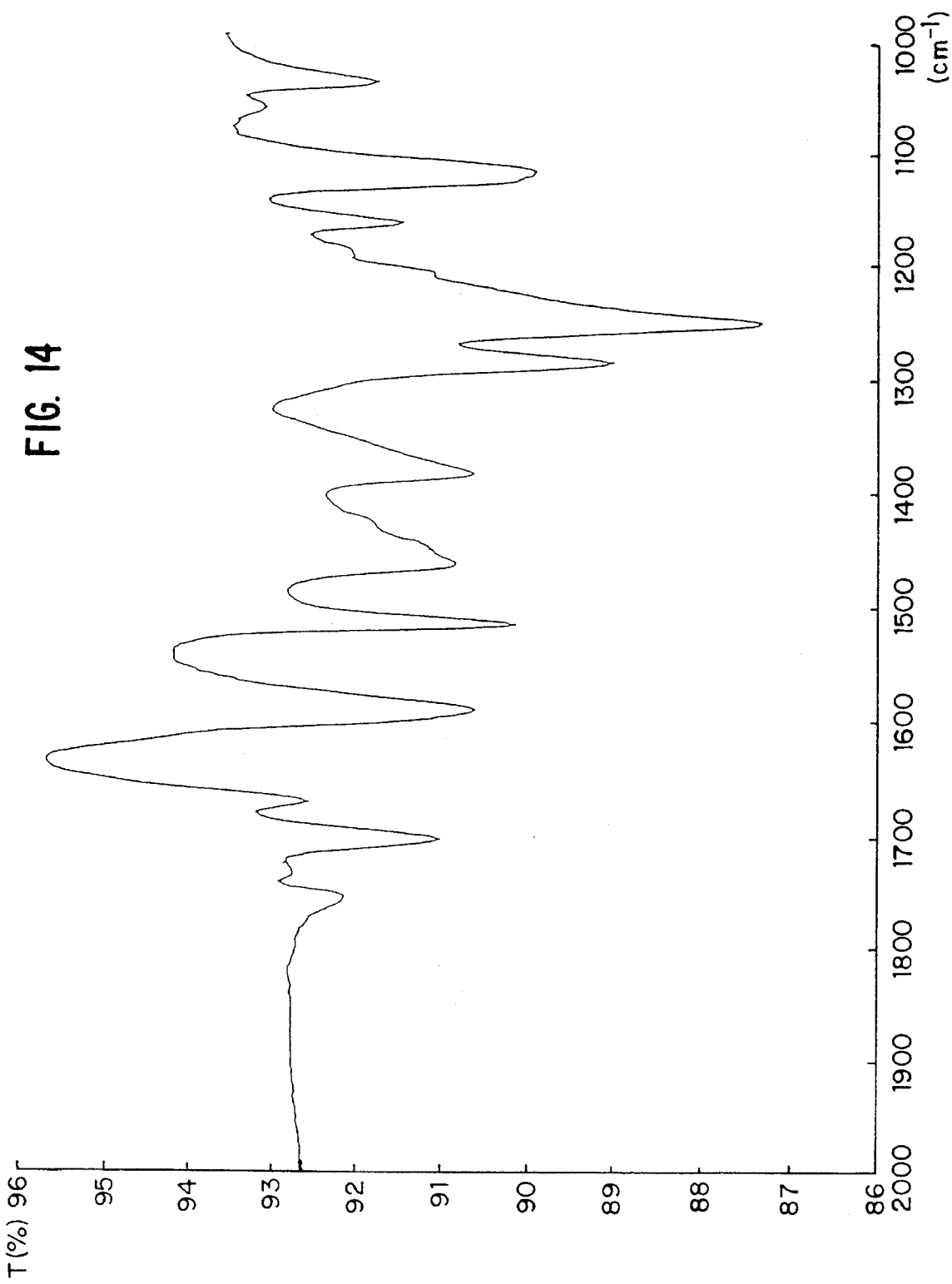
FIG. 14 shows the differential infrared absorption spectrum of CAMFE+egg yolk and egg yolk alone.

To further illustrate the present invention in greater detail, and not by way of limitation, the following Test Examples and Examples will be given.

Unless otherwise noted, all % in these Test Examples and Examples are by weight.

The extract, γ-OZ, CAFE, 24-MFE and CAMFE employed in Test Examples 1 to 4 and Examples 1 to 9 were prepared each in the following manner. The extract was prepared by subjecting rice bran to extracting with hexane; degumming, dewaxing and deacidifying the oily components thus obtained to thereby separate an edible oil; neutralizing the foots thus obtained, followed by distillation of the insoluble matters, washing with a solvent and treatment with an alumina column. As the γ-OZ, a commercially available product was used. CAFE and 24-MFE were prepared by repeatedly recrystallizing γ-OZ from acetone/methanol, acetone and ethyl acetate by reference to the method of Endo, Misu and Inaba et al. [Yukagaku (Oil Chemistry), 18, 63–67 (1969)]. CAMFE was prepared in accordance with the method described in JP-A- 61-243099.

Test Example 1

Comparison of various additives in ability to form cholesterol complex:

The extract, CAFE, 24-MFE and CAMFE were used as test samples. First, 0.33 mmol (201 mg) of CAFE and 0.33 mmol (129 mg) of cholesterol were dissolved in 100 ml of tetrahydrofuran. After adding 100 ml of water, the mixture was evaporated to dryness under reduced pressure. The dry product thus obtained was suspended in 100 ml of water, filtered and dried under reduced pressure (85° C., 2 hours) and the infrared absorption spectrum was measured. Other test samples were similarly treated and the infrared absorption spectra were measured. Table 1 shows the results.

The ability to form cholesterol complex was evaluated based on the results of the infrared absorption spectrometry. In Table 1, ⊙ means that a very strong ability to form cholesterol complex was observed, ○ means that a somewhat weaker ability to form cholesterol complex was observed.

TABLE 1

| Sample | IR of pure material | IR of preparation | Difference in wave number | Evaluation |
| --- | --- | --- | --- | --- |
| Extract | 1700 cm$^{-1}$ (CO) | 1700 cm$^{-1}$ (CO) | 0 | impossible |
|  | 1680 cm$^{-1}$ (CO) | 1680 cm$^{-1}$ (CO) | 0 |  |
| CAFE | 1675 cm$^{-1}$ (CO) | 1690 cm$^{-1}$ (CO) change in OH absorption | +15 cm$^{-1}$ | ⊙ |
| 24-MFE | 1695 cm$^{-1}$ (CO) | 1690 cm$^{-1}$ (CO) change in OH absorption | +5 cm$^{-1}$ | ○ |
| CAMFE | 1700 cm$^{-1}$ (CO) | 1700 cm$^{-1}$ (CO) | 0 | ⊙ |
|  | 1668 cm$^{-1}$ (CO) | 1673 cm$^{-1}$ (CO) change in OH absorption | +5 cm$^{-1}$ |  |

As a result, it was suggested that CAFE, 24-MFE and CAMFE were able to form cholesterol complex, though it was not judged by the infrared absorption spectrometry whether the extract was able to form cholesterol complex or not. However, the extract is assumed to be able to form cholesterol complex, since it is a mixture of CAFE, 24-MFE, campesterol, stigmasterol, etc. and CAFE and 24-MFE constituting the same form cholesterol complex. Further, the results of animal experiments, which will be described hereinafter, also support this assumption.

Test Example 2

Relationship between the degree of freeze-drying of CAMFE-treated egg yolk and migration of CAMFE into egg yolk layer:

(1) Preparation of Sample

To each of 5 egg yolk samples weighing 10 g, 260 mg of CAMFE was added and the mixture was stirred at 200 rpm with a mechanical stirrer for 1 hour at 25° C. Then, these samples were freeze-dried in such a manner as to give water losses of 50%, 40%, 30%, 20% and 10%. Table 2 shows the drying ratio of each sample.

TABLE 2

| Sample | Loss in egg yolk (%) |
| --- | --- |
| No. 1 | 51.0 |
| No. 2 | 41.6 |
| No. 3 | 29.6 |
| No. 4 | 18.8 |
| No. 5 | 10.7 |

(2) Procedure

Each sample thus dried was ground and sieved (22-mesh) to give a dry egg yolk powder. Then, water was added in an amount corresponding to the loss due to the freeze-drying (about 5, 4, 3, 2 and 1 g). The obtained mixture was stirred at 200 rpm with a mechanical stirrer for 1 hour. After adding about 8 g of water, it was further stirred at 500 rpm for 2 hours. A portion (9 g) of this mixture was centrifuged at 10,000 rpm for 30 minutes.

The egg yolk layer was extracted with chloroform (20 ml×1, 10 ml×2) and the extract was dried over magnesium sulfate (2 g) and then concentrated. The concentrate was dissolved in chloroform to give a volume of 10 ml. A 5 µl portion thereof was analyzed by HPLC to thereby determine the CAMFE content.

Table 3 shows the results wherein a content of CAMFE is expressed in a chart area (µg.sec).

Analytical conditions for HPLC were as follows.

Detector: UV absorptiometer (detection wavelength: 293 nm).

Column: Asahipak ODP-50, 4.6 mm (i.d.)×150 mm.

Column temp.: 45° C.

Mobile phase: acetonitrile/water=95/5.

TABLE 3

| Sample | Egg yolk layer |
| --- | --- |
| No. 1 | 7,680,942 |
| No. 2 | 7,623,906 |
| No. 3 | 2,386,327 |
| No. 4 | 1,265,665 |
| No. 5 | 905,997 |

With an increase in the degree of freeze-drying, CAMFE became liable to migrate into the egg yolk layer. Namely, it is considered that CAMFE would come in contact with oily components in the egg yolk with a decrease of water, thus being absorbed by the egg yolk. The migration ratio at a water loss of 40% or above was particularly high.

Test Example 3

Degree of migration of the extract, CAFE or CAMFE contained in freeze-dried egg yolk into egg yolk layer:

(1) Preparation of Sample

To 10 g of egg yolk, 260 mg of the extract, CAFE or CAMFE was added, respectively. Next, the mixture was stirred at 200 rpm with a mechanical stirrer at 25° C. for 1 hour and then freeze-dried (50% loss) to thereby give a sample.

(2) Procedure

Each sample was ground and sieved (22-mesh) to thereby give a dry egg yolk powder. Then water was added in an amount corresponding to the loss due to the freeze-drying (about 5 g in each case). The obtained mixture was stirred at 200 rpm with a mechanical stirrer for 1 hour. After adding about 8 g of water, it was further stirred at 500 rpm for 2 hours. A portion (9 g) of this mixture was centrifuged at 10,000 rpm for 30 minutes.

The precipitate layer was separated from the egg yolk layer by decantation and the egg yolk layer and the precipitate layer were extracted with chloroform (20 ml×1, 10 ml×2) and each extract was dried over magnesium sulfate (2 g) and then concentrated. Each concentrate was dissolved in chloroform to give a volume of 10 ml. A 5 µl portion thereof was analyzed by HPLC to thereby determine each additive. Table 4 shows the results wherein a content of an additive is expressed in a chart area (µg.sec).

Analytical conditions for HPLC were the same as those used in Test Example 2.

TABLE 4

| Sample | Egg yolk layer (A) | Precipitate layer (B) | A/B |
| --- | --- | --- | --- |
| extract-treated | 7,384,067 | 3,819,789 | 1.933 |
| CAFE-treated | 9,033,489 | 6,578,706 | 1.373 |
| CAMFE-treated | 7,680,942 | 7,868,723 | 0.976 |

It is considered that the extract and CAFE has strong affinities for the egg yolk layer in comparison with CAMFE.

Test Example 4

Degree of migration of the extract, CAFE or CAMFE contained in freeze-dried cow's milk into cow's milk layer:

(1) Preparation of Sample

To 100 g of cow's milk, 22 mg of the extract, CAFE or CAMFE was added, respectively. Next, the mixture was stirred at 200 rpm with a mechanical stirrer at 25° C. for 1 hour and then freeze-dried to give a sample.

(2) Procedure

To each sample, water was added in an amount corresponding to the loss due to the freeze-drying (about 88 g in each case). The obtained mixture was stirred at 500 rpm with a mechanical stirrer for 1 hour at 25° C. and centrifuged at 6,000 rpm for 30 minutes. The cow's milk layer and the precipitate layer were separated by decantation. The cow's milk layer was freeze-dried and, after adding 50 ml of chloroform, heated under reflux for 30 minutes. Then, it was dried over magnesium sulfate, filtered and concentrated. On the other hand, the precipitate layer as such was extracted with chloroform (20 ml×1, 10 ml×2). After filtering off the magnesium sulfate, the extract was concentrated. Each of these extracts was adjusted to a volume of 10 ml with chloroform. A 5 µl portion of each extract was analyzed by HPLC to thereby determine the amount of each additive. Table 5 shows the results wherein a content of an additive is expressed in a chart area (µg.sec).

Analytical conditions for HPLC were the same as those used in Test Example 2.

TABLE 5

| Sample | Cow's milk layer (A) | Precipitate layer (B) | A/B |
| --- | --- | --- | --- |
| extract-treated | 299,511 | 1,104,309 | 0.2712 |
| CAFE-treated | 166,548 | 1,100,244 | 0.1514 |
| CAMFE-treated | 24,517 | 1,057,800 | 0.0232 |

It is considered that CAMFE has a weak affinity for the cow's milk layer in comparison with CAFE.

Example 1

Evaluation of ability to form cholesterol complex in food:

CAFE and CAMFE were used as samples.

To 10 g of commercially available egg yolk, 200 mg of CAFE was added and the mixture was stirred at room temperature for 1 hour and freeze-dried to give a sample for infrared absorption spectrometry. Further, a sample containing CAMFE (210 mg) and a control sample were prepared in the same manner. Table 6 shows the results.

TABLE 6

| Sample | IR of complex | Differential spectrum of preparation | Evaluation |
| --- | --- | --- | --- |
| CAFE | 1690 cm$^{-1}$ (CO) | 1710 cm$^{-1}$ (CO) | ○ |
| CAMFE | 1673 cm$^{-1}$ (CO) | 1675 cm$^{-1}$ (CO) | ○ |

Based on these results, it is considered that CAFE and CAMFE form a complex with cholesterol contained in egg yolk. In the case of CAFE, the absorption of the CAFE complex was involved in the absorption of the background (1710 cm$^{-1}$), since the background could not be completely eliminated due to the inhomogeneities of the carrier, i.e., egg yolk. However, the peak assignable to the pure CAFE (1675 cm$^{-1}$) was not observed and thus it was judged that CAFE is able to form a cholesterol complex.

Example 2

Formation of cholesterol complex in egg yolk:

To 10 g of egg yolk, 260 mg of the extract, CAFE or CAMFE was added and the mixture was stirred at 200 rpm with the use of a mechanical stirrer at room temperature for 1, 5 or 20 hours, followed by freeze-drying. In each case, about 5 g of a freeze-dried egg yolk powder containing a cholesterol complex was obtained.

Example 3

Formation of cholesterol complex in cow's milk:

To 100 g of egg yolk, 10 or 500 mg of the extract, CAFE or CAMFE was added and the mixture was stirred at 200 rpm at room temperature for 1, 5 or 20 hours, followed by freeze-drying. In each case, about 12 g of a freeze-dried milk powder containing a cholesterol complex was obtained.

Example 4

Method for removing cholesterol from egg yolk combined with freeze-drying step:

To 10 g of egg yolk, 260 mg of the extract, CAFE or CAMFE was added, respectively, and the mixture was stirred at 200 rpm with the use of a mechanical stirrer at room temperature for 1, 10 or 20 hours, followed by freeze-drying.

The freeze-dried egg yolk thus obtained was ground and sieved (22-mesh) to give a dry egg yolk powder. Next, water was added in an amount corresponding to the loss due to the freeze-drying (about 5 g) and the resulting mixture was further stirred at 200 rpm with a mechanical stirrer for 2 hours. After adding about 3 or 8 g of water, it was stirred at 500 rpm for additional 30 minutes or 2 hours. A 6.5 g or 9 g portion of this water-reconstituted egg yolk was centrifuged.

Then, the precipitate layer was separated from the egg yolk layer by decantation and the egg yolk layer was freeze-dried. Thus, 1.94 to 2.37 g (77.6 to 94.8%) of a low-cholesterol egg yolk powder was obtained.

Table 7 shows the results of the enzymatic determination of cholesterol contained in the egg yolk layer and the precipitate layer prepared by stirring for 1 hour, adding 8 g of water and centrifuging 9 g of the water-reconstituted egg yolk.

TABLE 7

| Sample | Cholesterol conc. (mg/dl) |
| --- | --- |
| untreated yolk | |
| (yolk layer) | 171.23 (100%) |
| (precipitate layer) | 23.15 |
| Ext.-treated | |
| (yolk layer) | 145.35 (84.9%) |
| (precipitate layer) | 47.11 |
| CAFE-treated | |
| (yolk layer) | 113.64 (66.4%) |
| (precipitate layer) | 77.36 |
| CAMFE-treated | |
| (yolk layer) | 102.76 (60.0%) |
| (precipitate layer) | 86.39 |

By this method, cholesterol contained in the egg yolk was reduced by 20 to 40%.

Example 5

Method for removing cholesterol from cow's milk combined with freeze-drying step:

To 100 g of cow's milk, 10 or 500 mg of the extract, CAFE or CAMFE was added and the mixture was stirred at 200 rpm at room temperature for 1, 5 or 20 hours, followed by freeze-drying. Next, water was added in an amount corresponding to the loss due to freeze-drying (about 88 g) and the resulting mixture was further stirred at 200 rpm at room temperature for 1, 5 or 20 hours and then centrifuged.

Then cow's milk layer was separated from the precipitate layer by decantation and freeze-dried. Thus, 10.5 to 11.8 g (87.5 to 98.3%) of a low-cholesterol cow's milk powder was obtained.

When determined by the enzymatic method, it was found that cholesterol was reduced by 75 to 95%.

Example 6

Administration test of cholesterol complex-containing food by using rat:

As test samples, the extract, γ-OZ, CAFE, 24-MFE and CAMFE were employed.

<Test animal>
Species and strain: Slc:SD rat (SPF).
Sex: Male.
Age at purchase: 7 weeks.

<Test method>

(1) Classification and groups

Food: a powdery food containing 1% of cholesterol (hereinafter sometimes referred to simply as CHL) and 0.5% sodium cholate (CE-2, a product of Clea Japan Inc.).

(2) Test method and blood collection

Each test sample was added to the food at a ratio as specified in Table 8 and the animals were allowed to take it ad libitum. The body weight change and food intake were measured. After 7 days, the blood of each animal was taken from the abdominal aorta and the total cholesterol level in the serum was measured. Tables 9 to 11 show the results.

TABLE 8

| No. | Group | | No. of rats | Sample g/100 g CE-2 |
|---|---|---|---|---|
| 1 | Normal | | 8 | |
| 2 | Control | (CHL) | 8 | 1 |
| 3 | Ext./CHL | (0.5:1) | 8 | 1.713 |
| 4 | Ext./CHL | (1:1) | 8 | 2.562 |
| 5 | Ext./CHL | (2:1) | 8 | 4.186 |
| 6 | γ-OZ/CHL | (0.5:1) | 8 | 1.788 |
| 7 | γ-OZ/CHL | (1:1) | 8 | 2.576 |
| 8 | γ-OZ/CHL | (2:1) | 8 | 4.152 |
| 9 | CAFE/CHL | (0.5:1) | 8 | 1.780 |
| 10 | CAFE/CHL | (1:1) | 8 | 2.558 |
| 11 | CAFE/CHL | (2:1) | 8 | 4.166 |
| 12 | 24-MFE/CHL | (0.5:1) | 8 | 1.798 |
| 13 | 24-MFE/CHL | (1:1) | 8 | 2.594 |
| 14 | 24-MFE/CHL | (2:1) | 8 | 4.188 |
| 15 | CAMFE/CHL | (1:1) | 8 | 2.594 |

(3) Body weight is expressed by the mean ± standard deviation (g).

TABLE 9

| No. | Group | | Administration time (day) | | | |
|---|---|---|---|---|---|---|
| | | | 0 | 3 | 7 | 9 |
| 1 | Normal | | 269 ± 12 | 278 ± 13 | 296 ± 13 | 308 ± 15 |
| 2 | Control | (CHL) | 268 ± 10 | 272 ± 8 | 290 ± 11 | 306 ± 10 |
| 3 | Ext./CHL | (0.5:1) | 269 ± 08 | 271 ± 10 | 290 ± 21 | 298 ± 18 |
| 4 | Ext./CHL | (1:1) | 270 ± 09 | 270 ± 10 | 293 ± 18 | 305 ± 23 |
| 5 | Ext./CHL | (2:1) | 268 ± 10 | 273 ± 9 | 296 ± 19 | 302 ± 8 |
| 6 | γ-OZ/CHL | (0.5:1) | 268 ± 9 | 295 ± 41 | 301 ± 9 | 313 ± 6 |
| 7 | γ-OZ/CHL | (1:1) | 268 ± 10 | 274 ± 14 | 294 ± 10 | 311 ± 14 |
| 8 | γ-OZ/CHL | (2:1) | 267 ± 10 | 277 ± 15 | 295 ± 10 | 307 ± 9 |
| 9 | CAFE/CHL | (0.5:1) | 268 ± 9 | 270 ± 13 | 293 ± 14 | 307 ± 14 |
| 10 | CAFE/CHL | (1:1) | 270 ± 8 | 278 ± 5 | 299 ± 7 | 314 ± 8 |
| 11 | CAFE/CHL | (2:1) | 268 ± 11 | 267 ± 18 | 283 ± 20 | 299 ± 20 |
| 12 | 24-MFE/CHL | (0.5:1) | 268 ± 9 | 273 ± 17 | 291 ± 21 | 305 ± 16 |
| 13 | 24-MFE/CHL | (1:1) | 268 ± 9 | 273 ± 11 | 296 ± 5 | 312 ± 5 |
| 14 | 24-MFE/CHL | (2:1) | 270 ± 8 | 263 ± 14 | 280 ± 18 | 297 ± 21 |
| 15 | CAMFE/CHL | (1:1) | 267 ± 8 | 278 ± 11 | 298 ± 15 | 311 ± 15 |

(4) Food intake is expressed by the means ± standard deviation (g/animal/day).

TABLE 10

| No. | Group | | Administration time (day) | | |
|---|---|---|---|---|---|
| | | | 0–3 | 4–7 | 8–9 |
| 1 | Normal | | 19.4 ± 2.9 | 21.8 ± 3.2 | 25.3 ± 5.4 |
| 2 | Control | (CHL) | 16.0 ± 1.2 | 22.5 ± 2.9 | 27.3 ± 1.7 |
| 3 | CAFE/CHL | (0.5:1) | 18.5 ± 2.2 | 23.0 ± 1.5 | 27.6 ± 2.0 |
| 4 | CAFE/CHL | (1:1) | 17.2 ± 1.8 | 23.5 ± 1.9 | 26.4 ± 2.1 |
| 5 | ACFE/CHL | (2:1) | 15.6 ± 3.2 | 21.7 ± 1.5 | 28.6 ± 1.7 |
| 6 | 24-MFE/CHL | (0.5:1) | 17.4 ± 3.9 | 22.5 ± 2.1 | 26.6 ± 5.4 |
| 7 | 24-MFE/CHL | (1:1) | 17.0 ± 2.7 | 22.5 ± 2.7 | 28.5 ± 2.6 |
| 8 | 24-MFE/CHL | (2:1) | 13.3 ± 3.3 | 21.5 ± 3.1 | 26.4 ± 4.1 |
| 9 | Ext./CHL | (0.5:1) | 18.8 ± 4.5 | 23.5 ± 3.6 | 28.9 ± 5.0 |
| 10 | Ext./CHL | (1:1) | 19.5 ± 2.6 | 23.5 ± 2.0 | 26.4 ± 6.2 |
| 11 | Ext./CHL | (2:1) | 19.1 ± 1.8 | 21.9 ± 1.9 | 28.8 ± 3.8 |
| 12 | γ-OZ/CHL | (0.5:1) | 19.9 ± 1.5 | 22.6 ± 2.6 | 29.0 ± 2.5 |

TABLE 10-continued

| No. | Group | | Administration time (day) | | |
|---|---|---|---|---|---|
| | | | 0–3 | 4–7 | 8–9 |
| 13 | γ-OZ/CHL | (1:1) | 17.8 ± 3.0 | 23.2 ± 1.3 | 29.8 ± 4.9 |
| 14 | γ-OZ/CHL | (2:1) | 19.2 ± 2.4 | 22.3 ± 2.5 | 28.9 ± 4.1 |
| 15 | CAMFE/CHL | (1:1) | 17.8 ± 2.2 | 23.2 ± 2.2 | 27.1 ± 2.1 |

(5) Total cholesterol level in the serum is expressed by the mean ± standard deviation (mg/dl).

TABLE 11

| No. | Group | | Mean ± standard deviation |
|---|---|---|---|
| 1 | Normal | | 83.25 ± 15.39*** |
| 2 | Control | (CHL) | 176.13 ± 25.40 |
| 3 | Ext./CHL | (0.5:1) | 168.25 ± 28.36 |
| 4 | Ext./CHL | (1:1) | 128.51 ± 20.56*** |
| 5 | Ext./CHL | (2:1) | 110.82 ± 26.49*** |
| 6 | γ-OZ/CHL | (0.5:1) | 170.75 ± 38.04 |
| 7 | γ-OZ/CHL | (1:1) | 136.13 ± 28.56* |
| 8 | γ-OZ/CHL | (2:1) | 112.38 ± 21.68*** |
| 9 | CAFE/CHL | (0.5:1) | 174.13 ± 32.99 |
| 10 | CAFE/CHL | (1:1) | 122.88 ± 23.05*** |
| 11 | CAFE/CHL | (2:1) | 140.38 ± 29.96* |
| 12 | 24-MFE/CHL | (0.5:1) | 165.63 ± 33.75 |
| 13 | 24-MFE/CHL | (1:1) | 135.25 ± 28.09* |
| 14 | 24-MFE/CHL | (2:1) | 123.75 ± 23.37*** |
| 15 | CAMFE/CHL | (1:1) | 100.75 ± 8.01*** |

*P < 0.05; ***: P < 0.001.

As described above, increases in the total cholesterol level in the serum were significantly suppressed in the groups of CAFE/CHL (1:1), CAFE/CHL (2:1), 24-MFE/CHL (1:1), 24-MFE/CHL (2:1), extract/CHL (1:1), extract/CHL (2:1), γ-OZ/CHL (1:1), γ-OZ/CHL (2:1) and CAMFE/CHL (1:1). None of these additives caused any significant change in body weight or food intake. Thus, it can be concluded that they are applicable to foods without any problem.

Example 7

Administration test of egg yolk powder-containing food by using rat:

As test samples, the extract, γ-OZ, CAFE and CAMFE were employed.

<Test animal>
Species and strain: Slc:SD rat (SPF).
Sex: Male.
Age at purchase: 7 weeks.
<Test method>

(1) Preparation of egg yolk powder

To 2500 g of egg yolk, no additive or 50 g of each additive was added. After stirring with a mechanical stirrer for 1 hour, the mixture was freeze-dried. Thus, about 1250 g of a egg yolk powder with cholesterol complex formation was obtained.

(2) Food and group

Each egg yolk powder obtained in the above (1) was mixed with a 0.5% sodium cholate-containing food (CE-2) at a ratio of 1:1 and employed in a test wherein groups were classified as in Table 12.

TABLE 12

| No. | Group | No. of rats | Powdery food CE-2 (%) | Sodium cholate (%) | Yolk powder | Yolk powder with complex |
|---|---|---|---|---|---|---|
| 1 | Normal | 8 | 99.5 | 0.5 | — | — |
| 2 | Control | 8 | 49.5 | 0.5 | 50.0 | — |
| 3 | Extract | 8 | 49.5 | 0.5 | — | 50.0 |
| 4 | γ-OZ | 8 | 49.5 | 0.5 | — | 50.0 |
| 5 | CAFE | 8 | 49.5 | 0.5 | — | 50.0 |
| 6 | CAMFE | 8 | 49.5 | 0.5 | — | 50.0 |

(3) Test method and blood collection (3) Test method and blood collection

The rats were allowed to take each food as listed in Table 12 ad libitum for 3 days. On the days 2 and 3, the blood of each animal was collected from the tail vein. On the day 4 of the administration, the blood was collected from the abdominal aorta and the total cholesterol level in the serum was measured.

Further, the liver was taken out and the cholesterol level in the liver was measured. Tables 13 to 15 show the body weight gain, food intake, total cholesterol level in the serum and cholesterol level in the liver of the rats.

(4) Body weight and food intake are expressed by the mean ± standard deviation (g).

TABLE 13

| | | Body weight (g) | | Intake (g/animal/day) |
|---|---|---|---|---|
| No. | Group | day 0 | day 3 | days 0–3 |
| 1 | Normal | 275.3 ± 11.6 | 283.4 ± 9.9 | 19.9 ± 1.3 |
| 2 | Control | 274.6 ± 10.9 | 289.2 ± 14.4 | 16.5 ± 0.8 |
| 3 | Extract | 275.1 ± 10.2 | 291.6 ± 12.5 | 18.2 ± 1.3 |
| 4 | γ-OZ | 275.9 ± 9.6 | 292.2 ± 10.5 | 17.9 ± 1.8 |
| 5 | CAFE | 274.8 ± 9.9 | 287.2 ± 11.7 | 17.1 ± 0.2 |
| 6 | CAMFE | 274.7 ± 13.1 | 288.4 ± 13.2 | 17.3 ± 0.5 |

(5) The total cholesterol level in the serum is expressed by the mean ± standard deviation (mg/dl).

TABLE 14

| | | Total CHL level in serum (mg/dl) | | |
|---|---|---|---|---|
| No. | Group | day 0 | day 2 | day 3 |
| 1 | Normal | 65.3 ± 7.9*** | 66.6 ± 9.5*** | 63.8 ± 10.7 |
| 2 | Control | 90.0 ± 8.2 | 95.6 ± 9.0 | 68.8 ± 11.0 |
| 3 | Extract | 70.6 ± 9.2** | 70.8 ± 10.3*** | 55.7 ± 6.8* |
| 4 | γ-OZ | 71.3 ± 10.3** | 72.8 ± 8.8*** | 57.4 ± 7.5* |
| 5 | CAFE | 81.1 ± 11.7 | 81.4 ± 16.3* | 66.8 ± 16.0 |

TABLE 14-continued

| | | Total CHL level in serum (mg/dl) | |
|---|---|---|---|
| No. | Group | day 0 | day 2 | day 3 |
| 6 | CAMFE | 76.6 ± 10.7* | 74.5 ± 10.7*** | 56.4 ± 8.1* |

*: $P < 0.05$; : $P < 0.01$; *: $P < 0.001$.

(6) Liver weight (g) and the total cholesterol level in the liver are expressed by the mean ± standard deviation (mg/g, mg/total).

TABLE 15

| | | Liver weight | CHL | |
|---|---|---|---|---|
| No. | Group | (g) | (mg/g liver) | (mg/liver) |
| 1 | Normal | 11.4 ± 1.1 | 4.8 ± 0.8*** | 55.1 ± 11.3*** |
| 2 | Control | 12.7 ± 1.3 | 16.7 ± 1.2 | 213.1 ± 27.4 |
| 3 | Extract | 11.9 ± 0.6 | 8.1 ± 0.6*** | 98.5 ± 21.8*** |
| 4 | γ-OZ | 12.6 ± 0.6 | 8.2 ± 1.1*** | 104.0 ± 18.2*** |
| 5 | CAFE | 12.7 ± 0.9 | 14.1 ± 0.9*** | 179.2 ± 15.0** |
| 6 | CAMFE | 12.4 ± 0.7 | 10.1 ± 2.8*** | 124.9 ± 37.4*** |

*: $P < 0.05$; : $P < 0.01$; *: $P < 0.001$.

Example 8

Forced oral administration of egg yolk powder by using rat:

As test samples, the extract, γ-OZ, CAFE and CAMFE were employed.

<Test animal>
Species and strain: Slc:SD rat (SPF).
Sex: Male.
Age at purchase: 7 weeks.
<Test method>

(1) Food and group

The egg yolk powder and egg yolk powder with cholesterol complex formation, prepared in the same manner as the one described in Example 7, were each adjusted to a dose of 3 g/6 ml/animal with the use of purified water for injection and forcibly administered per os to the rats three times a day for 3 days.

On the days 2 and 3, the blood of each animal was collected from the tail vein. On the day 4 of the administration, the blood was collected from the abdominal aorta and the total cholesterol level in the serum was measured.

Further, the liver was taken out and the total cholesterol level in the liver was measured. Tables 16 to 18 show the body weight gain, food intake, total cholesterol level in the serum and cholesterol level in the liver of the rats.

(2) Body weight is expressed by the mean ± standard deviation (g).

TABLE 16

| No. | Group | Day 0 | Day 3 |
|---|---|---|---|
| 1 | Normal | 265.4 ± 8.1 | 277.6 ± 7.4 |
| 2 | Control | 264.3 ± 13.1 | 275.5 ± 13.1 |
| 3 | Extract | 263.5 ± 11.8 | 276.2 ± 12.8 |
| 4 | γ-OZ | 265.2 ± 13.3 | 271.5 ± 16.6 |
| 5 | CAFE | 266.5 ± 13.0 | 279.4 ± 14.2 |
| 6 | CAMFE | 262.3 ± 10.2 | 271.7 ± 14.2 |

(3) The total cholesterol level in the serum is expressed by the mean ± standard deviation (mg/dl).

TABLE 17

| | | Total CHL level in serum (mg/dl) | | |
|---|---|---|---|---|
| No. | Group | day 0 | day 2 | day 3 |
| 1 | Normal | 52.3 ± 6.4*** | 55.9 ± 5.0*** | 55.5 ± 5.2*** |
| 2 | Control | 67.6 ± 4.0 | 86.4 ± 10.5 | 70.4 ± 5.9 |
| 3 | Extract | 53.2 ± 6.4*** | 61.6 ± 5.6*** | 52.8 ± 6.9*** |
| 4 | γ-OZ | 54.4 ± 4.6*** | 62.1 ± 4.1*** | 47.4 ± 3.2*** |
| 5 | CAFE | 61.1 ± 7.0* | 78.9 ± 10.1 | 62.3 ± 6.5* |
| 6 | CAMFE | 67.6 ± 11.8 | 74.0 ± 8.1* | 59.6 ± 10.6* |

*: $P < 0.05$; : $P < 0.01$; *: $P < 0.001$.

(4) Liver weight (g) and the total cholesterol level in the liver are expressed by the mean ± standard deviation (mg/g, mg/total).

TABLE 18

| | | Liver weight | CHL | |
|---|---|---|---|---|
| No. | Group | (g) | (mg/g liver) | (mg/liver) |
| 1 | Normal | 8.7 ± 0.4*** | 5.2 ± 0.4*** | 45.2 ± 4.4*** |
| 2 | Control | 10.3 ± 0.8 | 11.2 ± 1.8 | 116.5 ± 23.9 |
| 3 | Extract | 9.8 ± 0.5 | 5.1 ± 0.6*** | 49.7 ± 8.2*** |
| 4 | γ-OZ | 9.6 ± 0.8 | 5.3 ± 0.4*** | 50.4 ± 5.3*** |
| 5 | CAFE | 10.3 ± 0.7 | 9.7 ± 0.7* | 99.8 ± 9.2 |
| 6 | CAMFE | 9.6 ± 0.7 | 7.0 ± 1.2 | 67.5 ± 15.2*** |

*: $P < 0.05$; : $P < 0.01$; *: $P < 0.001$.

As described above, all of the test samples significantly suppressed increase in the total cholesterol level in the serum and the total cholesterol level in the liver in Examples 6 to 8. The extract, γ-OZ and CAMFE showed particularly remarkable significant differences. None of these additives caused any significant difference in body weight gain and food intake.

Example 9

Forced administration test of cholesterol complex by using normal and diabetic rats:

As test samples, CAFE, the extract and CAMFE were employed.
<Test animal>
Species and strain: Slc:SD rat (SPF).
Sex: Male.
Age at purchase: 7 weeks.
<Test method>

(1) Preparation of diabetic rat 42 to 44 mg/kg of alloxan was intravenously administered to male Slc:SD rats aged 8 weeks to thereby give diabetic rats.

In the test, diabetic rats 13 weeks after the administration of alloxan were used.

(2) Labeled compound $^3$H-cholesterol (hereinafter referred to as $^3$H-CHL) purchased from Japan Isotope Association was used.

(3) Formation of liquid preparation to be administered $^3$H-CHL was mixed with the extract, CAFE or CAMFE each at a ratio of 1:2 and dissolved in chloroform. After evaporating to dryness under reduced pressure, each complex was obtained. This complex was suspended in 5% acacia and thus a liquid preparation to be administered was formed. In the liquid preparation, the concentration of CHL was adjusted to 20 mg/ml.

(4) Administration method

The $^3$H-CHL liquid preparation, extract/$^3$H-CHL liquid preparation, CAFE/$^3$H-CHL liquid preparation or CAMFE/$^3$H-CHL liquid preparation was orally administered to normal and diabetic rats in a dose of 5 ml/kg by using a sound. The administration radioactivity was adjusted to 3.7 MBq/kg. The animals were fasted for about 18 hours before the administration and, immediately after the administration, allowed to take food.

(5) Measurement of serum level

Two, four, and six hours after the administration, the blood of each rat was collected from the tail vein. Twenty-four hours after the administration, the blood was collected from the abdominal aorta. The collected blood was centrifuged (3,000 rpm, 15 min) at 4° C. to give the serum. To 100 µl of the serum, 1 ml of a tissue solubilizer SOLUENE-350 (PACKRAD) was added. After the completion of the dissolution, 9 ml of a scintillator ECONOFLUOR (Du Pont NEN Research Products) was added and the radioactivity was measured with a liquid scintillation counter (TRI-CARB 4530, PCAKRAD). Tables 19 and 20 show the results of the measurement of the serum $^3$H-CHL level.

TABLE 19

| | | Normal rat | | | | |
|---|---|---|---|---|---|---|
| | | No. of rats | Serum $^3$H-CHL level (µg/ml) | | | |
| No. | Group | | 2 hrs | 4 hrs | 6 hrs | 24 hrs |
| 1 | CHL | 3 | 34.2 | 26.6 | 16.6 | 11.6 |
| 2 | Ext./CHL | 3 | 20.3 | 16.7 | 14.4 | 10.3 |
| 3 | CAFE/CHL | 3 | 17.5 | 16.2 | 16.2 | 11.6 |
| 4 | CAMFE/CHL | 3 | 11.0 | 12.1 | 6.1 | 2.8 |

TABLE 20

| | | Diabetic rat | | | | |
|---|---|---|---|---|---|---|
| | | No. of rats | Serum $^3$H-CHL level (µg/ml) | | | |
| No. | Group | | 2 hrs | 4 hrs | 6 hrs | 24 hrs |
| 1 | CHL | 3 | 12.5 | 12.7 | 12.2 | 10.5 |
| 2 | Ext./CHL | 3 | 8.8 | 11.1 | 9.0 | 8.2 |
| 3 | CAFE/CHL | 3 | 10.9 | 11.1 | 11.6 | 6.8 |
| 4 | CAMFE/CHL | 3 | 4.6 | 4.1 | 2.4 | 2.8 |

As shown above, the serum CHL level was suppressed by administering the complexes of CHL with the test samples in Example 9. In particular, CAMFE showed a remarkable effect.

CAFE employed in the following Examples 10 to 19 was prepared by repeatedly recrystallizing, similar to the procedure as in Example 1. As the extract, an extract obtained by degumming and dewaxing oily components extracted from rice bran with a solvent, followed by treatment with an alkali, neutralization and solid/liquid separation, and distilling the residue followed by solvent-extraction and column treatment was employed.

Example 10

Production of mayonnaise by using rice bran component-containing fat and oil:

After stirring 6 g of egg yolk by using an eggbeater, 4.5 ml of rice vinegar was added thereto and mixed. Next, 30 ml of salad oil (a product of The Nissin Oil Mills, Ltd. containing 2% of the extract was slowly added to give a mayonnaise.

Example 11

Production of mayonnaise by using whole egg and/or egg yolk treated with rice bran component:

(1) Production of mayonnaise by using dry egg yolk

To 6 g of egg yolk, 312 mg of the extract[1] was added and mixed by stirring with an eggbeater, followed by freeze-drying. A 3 g portion of the extract-containing dry egg yolk thus obtained was weighed and put into a mortar, and 3 ml of water, 4.5 ml of rice vinegar and 30 ml of salad oil were slowly added with stirring to give a mayonnaise.

1): The amount of the added extract, i.e. 312 mg was determined by referring that 78 mg of cholesterol was contained in 6 g of egg yolk (13 mg/1 g of egg yolk).

The amount of the extract to be added was set to about twice as much on a molar basis.

(2) Production of mayonnaise by using egg yolk

To 6 g of egg yolk, 312 mg of the extract[1] was added and mixed by using an eggbeater. After adding and mixing 4.5 ml of rice vinegar, 30 ml of salad oil was slowly added to give a mayonnaise.

Example 12

Production of mayonnaise by using whole egg and/or egg yolk treated with rice bran component and rice bran component-containing fat and oil:

(1) Production of mayonnaise by using extract-containing dry egg yolk

A 3 g portion of the extract-containing dry egg yolk obtained in the same manner as in Example 11 (1) was weighed and put into a mortar, and 3 ml of water and 4.5 ml of rice vinegar was added thereto. Next, 30 ml of the extract-containing salad oil obtained in the same manner as in Example 10 was slowly added to give a mayonnaise.

(2) Production of mayonnaise by using egg yolk

To 6 g of egg yolk, 312 mg of the extract[1] was added and mixed by using an eggbeater. After adding and mixing 4.5 ml of rice vinegar, 30 ml of the extract-containing salad oil obtained in the same manner as in Example 10 was slowly added to give a mayonnaise.

Example 13

Production of mayonnaise by using CAFE-containing fat and oil:

The procedures of Examples 10, 11 and 12 were repeated but substituting the extract with CAFE to produce mayonnaises.

Example 14

Forced oral administration test of mayonnaise produced by using rice bran component-containing fat and oil:
<Test animal>
Species and strain: Jcl:SD rat (SPF).
Sex: Male.
Age at purchase: 7 weeks.
<Test method>

(1) Preparation of diabetic rat

To male Jcl:SD rats aged 8 weeks, 42 to 44 mg/kg of alloxan was intravenously administered to give diabetic rats.

In the test, diabetic rats 13 weeks after the administration of alloxan were used.

(2) Production of mayonnaise

To 6 g of egg yolk, 1,050 mg of cholesterol was added and mixed by using an eggbeater and 4.5 ml of rice vinegar was added thereto. Then, 30 ml of salad oil containing 7% of the extract was slowly added to give a mayonnaise. The mayonnaise of the control group was produced by the similar method.

(3) Administration method and blood collection

The control mayonnaise prepared above was forcibly administered per os to the rats in a dose of 9 g/kg twice a day for 2 days. At 9:00 a.m. on the day 3, each mayonnaise was forcibly administered per os to the rats in the same dose. After 4 and 8 hours, the blood of each animal was collected from the tail vein. After 24 hours, the blood was collected from the abdominal aorta and the total cholesterol level in the serum was measured.

Example 15

Forced oral administration test of mayonnaise produced by using extract-containing egg yolk:
<Test animal>
Species and strain: Crj:SD rat (SPF).
Sex: Male.
Age at purchase: 7 weeks.
<Test method>

(1) Labeled compound $^3$H-cholesterol (hereinafter referred to as $^3$H-CHL) and $^{14}$C-cholesterol (hereinafter referred to as $^{14}$C-CHL) purchased from Japan Isotope Association were used.

(2) Preparation of dry egg yolk 1.5 ml of $^{14}$C-CHL (9.25 MBq/6.25 ml ethanol solution) and 0.5 ml of distilled water were introduced into a 50 ml round-bottom flask and the ethanol was evaporated under reduced pressure. Next, 1 ml of distilled water and 4 g of egg yolk were added thereto. In the case of the extract/$^{14}$C-CHL group, 209.2 mg of the extract[1] was further added thereto. After stirring, each mixture was frozen with dry ice/ethanol and freeze-dried for about 8 hours.

1): The amount of the added extract, i.e. 209.2 mg was determined by referring that 52.3 mg of cholesterol was contained in 4 g of egg yolk (13.08 mg/1 g of egg yolk). The amount of the extract to be added was set to about twice as much on a molar basis.

(3) Production of mayonnaise

A 1 g portion of the $^{14}$C-CHL or extract/$^{14}$C-CHL-containing dry egg yolk was weighed and put into a mortar. Then, 1 ml of water, 9 ml of salad oil and 1.5 ml of rice vinegar were slowly added and stirred to give a mayonnaise. The radioactivity (Bq/g) of the mayonnaise was measured with a liquid scintillator by sampling part of the mayonnaise.

(4) Preparation of cholesterol suspension for tail vein administration

A 35 µl portion of $^3$H-CHL[1,2,6,7-3H-(N)-] was pipetted into a 10 ml test tube with a glass stopper and evaporated to dryness under a nitrogen atmosphere. Then, it was dissolved in 200 µl of 95% ethanol. Then, it was suspended in physiological saline and the total volume was adjusted to 4 ml.

(5) Administration method

From the day of the administration, the rats were transferred into an RI feeding room and individually placed in stainless metabolism cages. At 10:00 a.m., the $^3$H-CHL suspension was intravenously administered through the tail vein in a dose of 2.5 ml/kg. Immediately thereafter, the $^{14}$C-CHL or the extract/$^{14}$C-CHL containing mayonnaise was orally administered in a dose of 10 g/kg by using a sound. The food was taken away from the cage at 4:00 p.m. on the day before the administration (water was given without restriction). Feeding was started again 6 hours after the administration. Then, 2, 4, 6, 8, 10, 24, 48 and 72 hours after the administration, the blood of each animal was collected from the tail vein. Further, 96 hours after the administration, the blood was taken from the abdominal aorta under etherization. After collecting, the blood was centrifuged to give the serum.

(6) Measurement of serum cholesterol level

To 100 mg of the serum, 1 ml of a tissue dissolution agent SOLUENE-350 (PACKRAD) was added. After the completion of the dissolution, 9 ml of a scintillator ECONOFLUOR (Du Pont NEN Research Products) was added and the radioactivity was measured with a liquid scintillation counter (TRI-CARB 4530, PACKRAD).

(7) Measurement of cholesterol absorption ratio

To 100 mg of the serum, 1 ml of the tissue dissolution agent SOLUENE-350 was added. Next, 9 ml of scintillator was further added thereto and the $^{14}C$ and $^{3}H$ radioactivities were measured with a liquid scintillation counter. Then, the absorption ratio of cholesterol ($^{14}C/^{3}H \times 100$) was determined.

Example 16

Forced oral administration test of mayonnaise by using extract-containing egg yolk:

The procedure of Example 14 was repeated but varying Example 14 <Test method> (2) and (3) as follows.

(2) Production of mayonnaise

To 6 g of egg yolk, 1,050 mg of cholesterol and 2,100 mg of the extract were added and mixed by using an eggbeater. Then, 4.5 ml of rice vinegar was added and 30 ml of salad oil was further added slowly to give a mayonnaise. The mayonnaise of the control group was produced in the similar manner.

(3) Administration method and blood collection

The mayonnaise of the control group (9 g/kg) or the extract-treated mayonnaise (10 g/kg) prepared above was orally administered to the animals twice a day for 2 days.

Example 17

Forced oral administration test of mayonnaise produced by using rice bran component-treated whole egg and/or egg yolk and rice bran component-containing fat and oil:

The procedure of Example 15 was repeated but varying Example 15 <Test method> (3) as follows.

(3) Production of mayonnaise

A 1 g portion of the $^{14}C$-CHL or $^{14}C$-CHL-added dry egg yolk was weighed and put into a mortar. Then, 1 ml of water, 9 ml of salad oil containing 2% of the extract and 1.5 ml of rice vinegar were slowly added with stirring to give a mayonnaise. The radioactivity (Bq/g) of the mayonnaise was measured with a liquid scintillator by sampling part of the prepared mayonnaise.

Example 18

Forced oral administration test of mayonnaise produced by using rice bran component-treated whole egg and/or egg yolk and rice bran component-containing fat and oil:

The procedure of Example 16 was repeated but varying Example 16 <Test method> (2) as follows.

(2) Production of mayonnaise

To 6 g of egg yolk, 1,050 mg of cholesterol and 2,100 mg of the extract were added and mixed by using an eggbeater. After adding 4.5 ml of rice vinegar, 30 ml of salad oil containing 7% of the extract was further added slowly to give a mayonnaise. The mayonnaise of the control group was produced in the same manner.

Example 19

Forced oral administration test of mayonnaise produced by using rice bran component-treated whole egg and/or egg yolk and rice bran component-containing fat and oil:

The procedure of Example 15 was repeated but varying Example 15 <Test method> (3) as follows.

(3) Production of mayonnaise

A 1 g portion of $^{14}C$-CHL or the extract/$^{14}C$-CHL-added dry egg yolk was weighed and put into a mortar. Then, 1 ml of water, 9 ml of salad oil containing 2% of the extract and 1.5 ml of rice vinegar were slowly added with stirring to thereby give a mayonnaise. The radioactivity (Bq/g) of the mayonnaise was measured with a liquid scintillator by sampling part of the prepared mayonnaise.

Table 21 shows the results of the measurement of the total cholesterol level in the serum in Examples 14, 16 and 18.

TABLE 21

| Group | No. of rats | Content (%) CHL | Content (%) Ext. | Dose (g/kg) | Total CHL in blood (mg/dl) before 0 | after (hrs) 4 | after (hrs) 8 | after (hrs) 24 |
|---|---|---|---|---|---|---|---|---|
| Control | 8 | 2.7 | — | 9 | 218 ± 70 | 679 ± 204 | 680 ± 162 | 550 ± 284 |
| Ex. 14 | 8 | 2.7 | 5.0 | 9 | 219 ± 69 | 556 ± 286 | 520 ± 113* | 458 ± 170 |
| Ex. 16 | 8 | 2.7 | 5.0 | 10 | 222 ± 66 | 540 ± 135 | 515 ± 100* | 444 ± 230 |
| Ex. 18 | 8 | 2.7 | 10.0 | 10 | 220 ± 60 | 390 ± 103** | 321 ± 115*** | 263 ± 141* |

*: $P < 0.05$; : $P < 0.01$; *: $P < 0.001$.

The total cholesterol level in the serum is expressed by the mean ± standard deviation (mg/dl).

The data obtained 8 hours after the final administration as given in Table 21 indicate that in the mayonnaise produced by adding the extract-containing salad oil to egg yolk (corresponding to the mayonnaise described in Example 10) and the mayonnaise produced by adding the extract to egg yolk and then adding salad oil thereto [corresponding to the mayonnaise described in Example 11 (2)], the total cholesterol level in the serum of the extract-treated egg yolk/salad oil was obviously lowered compared with the control case with the use of egg yolk/salad oil.

Compared with the control case with the use of egg yolk/salad oil, the total cholesterol level in the serum was remarkably lowered in the case of the mayonnaise obtained from the extract-treated egg yolk/extract-containing salad oil [corresponding to the mayonnaise described in Example 12 (2)].

Table 22 shows the area under curve of the serum total cholesterol level curves (0–96 hours) of Examples 15, 17 and 19 expressed in the mean + standard deviation ($\mu g \cdot hr \cdot ml^{-1}$).

TABLE 22

| Group | No. of rats | Content CHL (%) | Content Ext. (%) | Dose (g/kg) | Area Under Curve (0–96 hrs) calcd. ($\mu g \cdot hr \cdot ml^{-1}$) | Area Under Curve (0–96 hrs) ratio (%) |
|---|---|---|---|---|---|---|
| Control | 3 | 0.26 | — | 10 | 1472.3 ± 207.0 | 100 |
| Ex. 15 | 3 | 0.26 | 1.04 | 10 | 1274.3 ± 234.0 | 86.6 |
| Ex. 17 | 3 | 0.26 | 1.80 | 10 | 1261.8 ± 212.6 | 85.7 |
| Ex. 19 | 3 | 0.26 | 2.84 | 10 | 729.3 ± 117.7** | 49.5 |

**: $P < 0.01$.

The data given in Table 22 indicate that the use of the extract-treated, freeze-dried egg yolk/salad oil suppressed the absorption of cholesterol by 13.4% compared with the case wherein the freeze-dried egg yolk/salad oil was used, and the use of the extract-containing salad oil suppressed the absorption of cholesterol by 14.3% compared with the case where the freeze-dried egg yolk/salad oil was used.

When the above-mentioned methods were employed in combination, that is to say, the extract-treated, freeze-dried egg yolk/extract-containing oil was used, the absorption of cholesterol was suppressed by 50.5% compared with the case where the freeze-dried egg yolk/salad oil was used, showing a remarkable synergistic effect.

Figure 15:
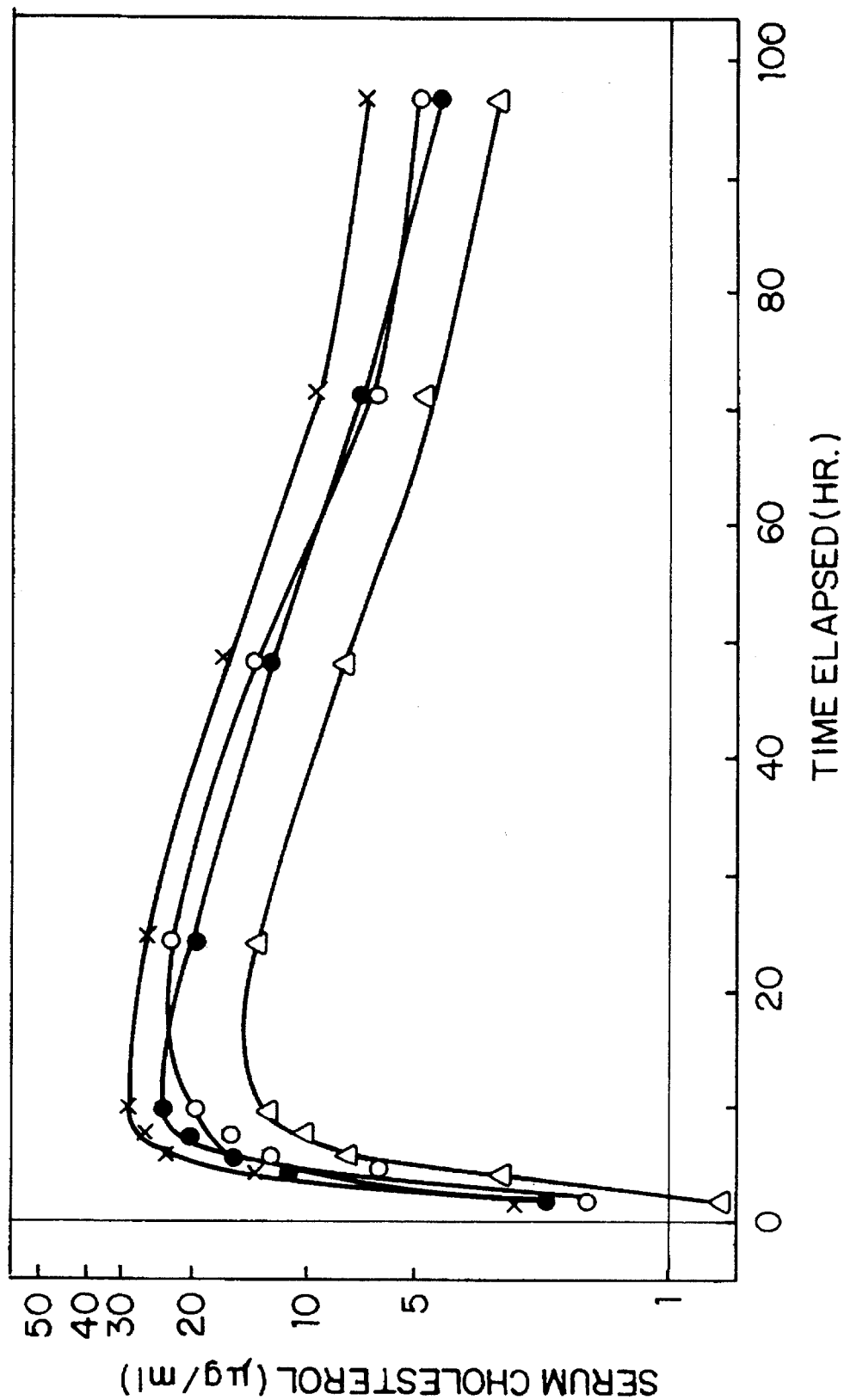
FIG. 15 is a graph showing the serum cholesterol level within a period of 2 to 72 hours after the administration of various mayonnaises, wherein -△- stands for the data of a mayonnaise produced by using extract-treated, freeze-dried egg yolk/extract-containing salad oil; -●- stands for the data of a mayonnaise produced by using extract-treated, freeze-dried egg yolk/salad oil; -○- stands for the data of a mayonnaise produced by using freeze-dried egg yolk/extract-containing salad oil; and -x- stands for the data of a mayonnaise produced by using freeze-dried egg yolk/salad oil.
Figure 16:
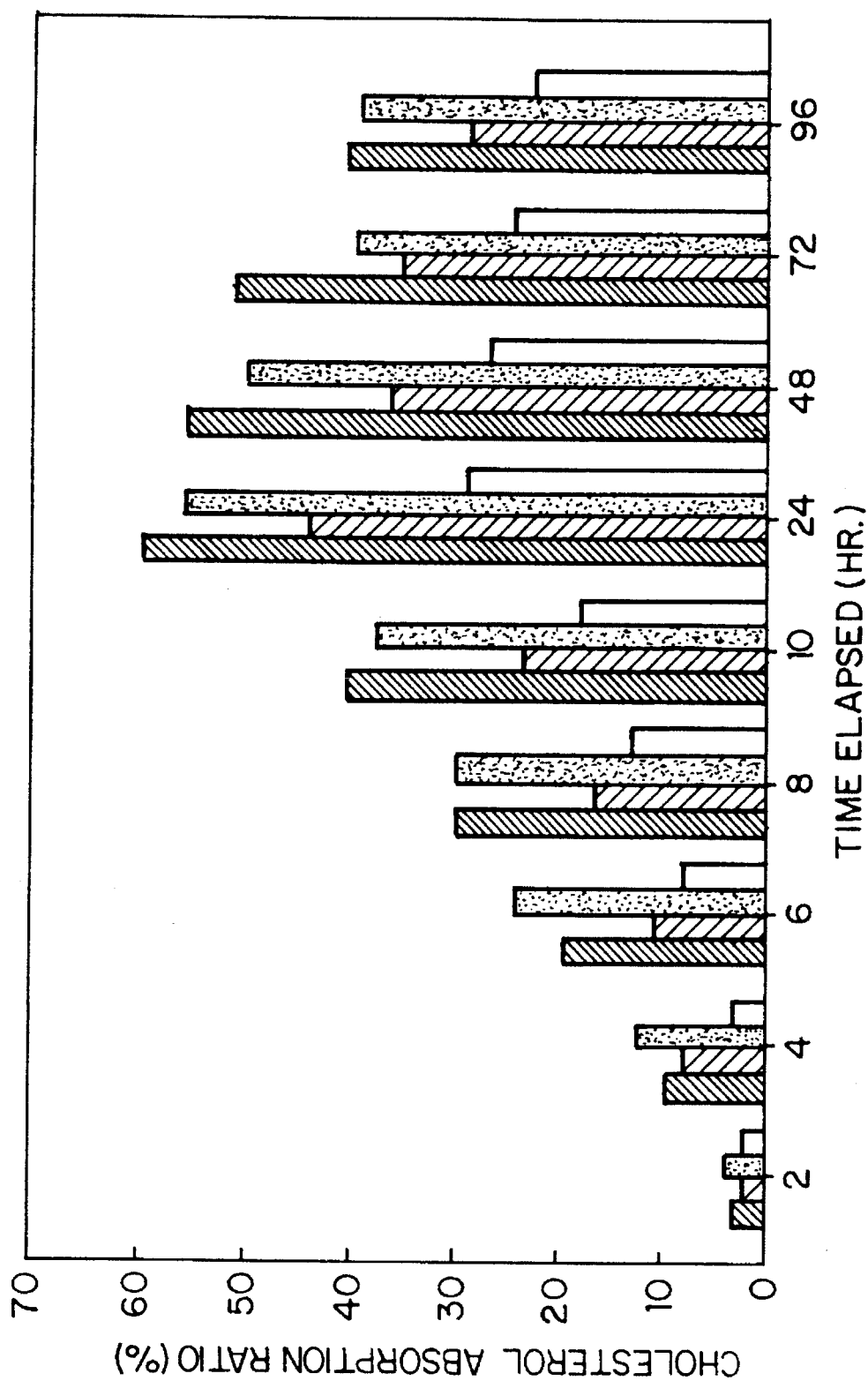
FIG. 16 is a graph showing cholesterol absorption ratio within a period of 2 to 96 hours after the administration of various mayonnaises, wherein the bars respectively stand for, from left to right, the data of a mayonnaise produced by using freeze-dried egg yolk/salad oil, a mayonnaise produced by using extract-treated, freeze-dried egg yolk/salad oil, a mayonnaise produced by using freeze-dried egg yolk/extract-containing salad oil and a mayonnaise produced by using extract-treated, freeze-dried egg yolk/extract-containing salad oil.

FIG. 15 shows the serum cholesterol level within a period of 2 to 72 hours after the administration, while FIG. 16 shows the cholesterol absorption within a period of 2 to 96 hours after the administration.

These FIGS. 15 and 16 indicate that the serum cholesterol level and cholesterol absorption ratio after 24 hours from the administration were in the following order. In particular, the case with the use of the extract-treated, freeze-dried egg yolk/extract-containing salad oil showed extremely low values.

1. Use of extract-treated, freeze-dried egg yolk/extract-containing salad oil.
2. Use of extract-treated, freeze-dried egg yolk/salad oil.
3. Use of freeze-dried egg yolk/extract-containing salad oil.
4. Use of freeze-dried egg yolk/salad oil (control).

When the extract was substituted with CAFE and the total serum cholesterol level and the area under curve thereof (0–96 hours) were measured in the same manner as those of Examples 14 to 19, the obtained results were similar to the data obtained in Examples 14 to 19.

Example 20

Method for producing cake:

To 72 g of egg yolk or the extract-containing egg yolk, 36 g of wheat flour, 15 g of sugar and 1 g of baking powder were added at once and mixed. The obtained mixture was baked in an oven at 160° C. for 40 minutes. This cake contained 60 g of egg yolk per 100 g.

Example 21

Effect of the intake of cake produced by using extract-containing egg yolk on serum cholesterol:
<Test animal>
  Species and strain: Slc:SD rat (SPF).
  Sex: Male.
  Age at purchase: 7 weeks.
<Test method>

(1) Group

| Group | No. of rats | Composition of food (g) Cake | Composition of food (g) CE-2 |
|---|---|---|---|
| Treated control | 10 | 20 | 10 |
| Control | 10 | freely taking solid CE-2 | |
| Ext.-containing | 10 | 20 | 10 |

(2) Test method and blood collection

To the male Slc:SD rats (SPF, aged 8 weeks), 42 to 44 mg/kg of alloxan was intravenously administered. From 11 weeks thereafter, 20 g of the egg yolk-containing cake and 4 pellets (about 10 g) of a solid food CE-2 were given to the animals to thereby prepare hypercholesterolemia rats.

The animals were fed for 10 days by giving 20 g of the cake produced by adding 2% (based on the egg yolk weight) of the extract and 4 pellets (about 10 g) of the solid food CE-2. On the days 5 and 10, the blood of each animal was collected from the tail vein and the total CHL in the serum was measured.

The total cholesterol level in the serum is expressed by the mean ± standard deviation (mg/dl).

TABLE 23

Total CHL in serum of rat after administering cake produced by using extract-containing egg yolk

| Group | No. of rats | Total CHL level in serum (mg/dl) Day 0 | Total CHL level in serum (mg/dl) Day 5 | Total CHL level in serum (mg/dl) Day 10 |
|---|---|---|---|---|
| Treated control | 10 | 563.3 ± 402.2 | 659.6 ± 433.5 (0) | 760.3 ± 443.0 (0) |
| Control | 10 | 547.5 ± 355.9 | 202.4 ± 58.9 (100)** | 227.9 ± 100.5 (100)** |
| Ext.-containing | 10 | 568.8 ± 360.6 | 254.9 ± 162.1 (88)* | 267.2 ± 192.7 (93)** |

Mean ± standard deviation; *: $P < 0.05$; **: $P < 0.01$.
( ): Suppression ratio.

[Industrial Applicability]

According to the present invention, cholesterol contained in a food can be reduced and the absorption thereof by a living body can be prevented. Thus, a food additive and a food, which are useful in inhibiting the accumulation of cholesterol in the living body and in preventing arteriosclerosis, can be obtained. According to the present invention, mayonnaises having an effect of lowering blood cholesterol level or suppressing an increase of blood cholesterol level can be obtained.

We claim:

1. A method of removing cholesterol which comprises adding an additive comprising rice bran components, derivatives of rice bran components, or rice bran components and derivatives of rice bran components as an active component to a cholesterol-containing food to form a cholesterol complex, and removing said cholesterol complex therefrom.

2. A cholesterol complex comprising, cholesterol and an additive selected from the group consisting of a rice bran component, a derivative of a rice bran component, and a rice bran component and a derivative of a rice bran component.

3. A food obtained by a process of removing cholesterol comprising the steps of:

adding an additive comprising rice bran components, derivatives of rice bran components, or rice bran components and derivatives of rice bran components as an active component to a cholesterol-containing food to form a cholesterol complex, and removing said cholesterol complex therefrom.

* * * * *